US010000567B2

(12) United States Patent
Ellis et al.

(10) Patent No.: US 10,000,567 B2
(45) Date of Patent: Jun. 19, 2018

(54) HUMANIZED ANTIBODIES TO CLUSTER OF DIFFERENTIATION 3 (CD3)

(71) Applicant: Therapix Biosciences Ltd., Ness Ziona (IL)

(72) Inventors: Ronald Ellis, Jerusalem (IL); Michael Tal, Kfar Bilu (IL); Sarit Samira, Nes Ziona (IL); Nurit Rachamim, Rishon LeZiyyon (IL); Timothy David Jones, Babraham (GB); Francis Joseph Carr, Balmedie (GB); Shahar Dotan, Omer (IL)

(73) Assignee: Therapix Biosciences Ltd., Tel Aviv (IL)

( * ) Notice: Subject to any disclaimer, the term of this patent is extended or adjusted under 35 U.S.C. 154(b) by 230 days.

(21) Appl. No.: 14/408,128

(22) PCT Filed: Mar. 12, 2013

(86) PCT No.: PCT/IB2013/001165
§ 371 (c)(1),
(2) Date: Dec. 15, 2014

(87) PCT Pub. No.: WO2013/186613
PCT Pub. Date: Dec. 19, 2013

(65) Prior Publication Data
US 2015/0175699 A1 Jun. 25, 2015

Related U.S. Application Data

(60) Provisional application No. 61/659,717, filed on Jun. 14, 2012.

(51) Int. Cl.
*C07K 16/28* (2006.01)
*A61K 39/00* (2006.01)

(52) U.S. Cl.
CPC .... *C07K 16/2809* (2013.01); *A61K 2039/505* (2013.01); *C07K 2317/24* (2013.01); *C07K 2317/31* (2013.01); *C07K 2317/56* (2013.01); *C07K 2317/565* (2013.01); *C07K 2317/567* (2013.01); *C07K 2317/622* (2013.01); *C07K 2317/624* (2013.01)

(58) Field of Classification Search
CPC .......... C07K 16/2809; C07K 2317/565; C07K 2317/567; C07K 2317/24
USPC ..................... 424/133.1; 530/387.3
See application file for complete search history.

(56) References Cited

U.S. PATENT DOCUMENTS

| | | | |
|---|---|---|---|
| 4,458,066 A | 6/1984 | Caruthers et al. | |
| 4,816,567 A | 3/1989 | Cabilly et al. | |
| 5,885,573 A * | 3/1999 | Bluestone | C07K 16/2809 424/133.1 |
| 6,491,916 B1 * | 12/2002 | Bluestone | C07K 16/2809 424/133.1 |
| 6,632,927 B2 * | 10/2003 | Adair | C07K 16/18 424/133.1 |
| 6,750,325 B1 * | 6/2004 | Jolliffe | C07K 16/18 424/130.1 |
| 7,883,703 B2 | 2/2011 | Weiner et al. | |
| 7,993,641 B2 | 8/2011 | Waldemann et al. | |
| 8,101,722 B2 * | 1/2012 | Kufer | C07K 16/2803 530/387.3 |
| 8,663,634 B2 * | 3/2014 | Koenig | A61K 38/28 424/130.1 |
| 9,056,906 B2 * | 6/2015 | Koenig | C07K 16/2809 |
| 9,493,563 B2 * | 11/2016 | Blein | C07K 16/2896 |
| 2003/0108548 A1 * | 6/2003 | Bluestone | C07K 16/2809 424/144.1 |
| 2006/0002933 A1 * | 1/2006 | Bluestone | C07K 16/2809 424/144.1 |
| 2006/0292142 A1 * | 12/2006 | Bluestone | C07K 16/2809 424/144.1 |
| 2007/0077246 A1 * | 4/2007 | Koenig | A61K 38/28 424/144.1 |
| 2008/0095766 A1 * | 4/2008 | Koenig | C07K 16/2809 424/133.1 |
| 2008/0206239 A1 | 8/2008 | Jones | |
| 2008/0299137 A1 * | 12/2008 | Svendsen | C07K 16/2809 424/178.1 |
| 2009/0252748 A1 * | 10/2009 | Mi | C07K 16/2803 424/172.1 |
| 2010/0015142 A1 * | 1/2010 | Koenig | C07K 16/2809 424/133.1 |

(Continued)

FOREIGN PATENT DOCUMENTS

| | | |
|---|---|---|
| EP | 1400534 | 3/2004 |
| EP | 2080138 | 7/2009 |

(Continued)

OTHER PUBLICATIONS

Dufner (Trends Biotechnol. 24(11):523-29 (2006)).*
Ablamunits et al. Human Immunology 69 (2008) 732-736.*
Alegre et al. J Immunol 1992; 148:3461-3468.*
Hsu et al. Transplantation. Aug. 27, 1999;68(4):545-54 (Abstract).*
Huang et al. Zhonghua Yi Xue Za Zhi. Mar. 1, 2011;91(8):516-9. (Abstract).*
Jolliffe Int Rev Immunol. 1993;10(2-3):241-50 (Abstract).*
Li et al. International Immunopharmacology 6 (2006) 880-891.*
Popma et al. International Immunopharmacology 5 (2005) 155-162.*
Richards et al. [Cancer Research 59, 2096-2101, May 1, 1999].*
Woodle et al. J Immunol 1992; 148:2756-2763.*
Xu et al. Cellular Immunology 200, 16-26 (2000).*
Zhao et al. (J Immunother 2015;38:217-228).*

(Continued)

*Primary Examiner* — Lynn A Bristol
(74) *Attorney, Agent, or Firm* — Fish & Richardson P.C.

(57) ABSTRACT

Humanized monoclonal antibodies (mAbs) or fragments thereof, to human Cluster of Differentiation 3 (CD3), which confer improved immune stimulation and stability, are disclosed. Pharmaceutical compositions comprising said mAbs and methods of treatment and optionally also prevention of diseases and disorders, such as autoimmune disorders, infectious diseases, and transplant rejection, that are susceptible to amelioration by binding to CD3, are also disclosed.

19 Claims, 14 Drawing Sheets

(56) References Cited

U.S. PATENT DOCUMENTS

| | | | | |
|---|---|---|---|---|
| 2012/0321626 | A1* | 12/2012 | Zhou | C07K 14/705 424/136.1 |
| 2013/0034547 | A1* | 2/2013 | Kelly | C07K 1/1077 424/133.1 |
| 2015/0056206 | A1* | 2/2015 | Zhou | C07K 14/705 424/136.1 |
| 2015/0118252 | A1* | 4/2015 | Ho | C07K 16/2809 424/173.1 |
| 2015/0133640 | A1* | 5/2015 | Blein | C07K 16/2896 530/387.3 |
| 2016/0046714 | A1* | 2/2016 | Koenig | C07K 16/2809 424/133.1 |
| 2016/0289324 | A1* | 10/2016 | Moore | C07K 16/28 |
| 2016/0355588 | A1* | 12/2016 | Ng | C07K 16/2803 |
| 2016/0355592 | A1* | 12/2016 | Sagert | C07K 16/2842 |
| 2017/0002060 | A1* | 1/2017 | Bolen | C07K 16/00 |
| 2017/0051044 | A1* | 2/2017 | Chan | C07K 16/00 |

FOREIGN PATENT DOCUMENTS

| | | |
|---|---|---|
| WO | WO 2005/048935 | 6/2005 |
| WO | WO 2007107764 A1 * | 9/2007 |
| WO | WO 2009024771 A2 * | 2/2009 |
| WO | WO 2011/135544 | 11/2011 |
| WO | WO-2016180721 A1 * | 11/2016 |

OTHER PUBLICATIONS

Belghith et al., "TGF-bold beta-dependent mechanisms mediate restoration of self-tolerance induced by antibodies to CD3 in overt autoimmune diabetes," Nat. Med., Sep. 2003, 9:1202-8.

Chatenoud et al., "CD3 antibody-induced dominant self tolerance in overtly diabetic NOD mice," J. Immunol., Mar. 1997, 158:2947-2954.

Chatenoud, "CD3-specific antibody-induced active tolerance: from bench to bedside," Nat. Rev. Immunol., Feb. 2003, 3:123-32.

Herold et al, "Anti-CD3 monoclonal antibody in new-onset type 1 diabetes mellitus," N. Engl. J. Med., May 2002, 346:1692-82.

Hill et al., "The relationship between predicted peptide—MHC class II affinity and T-cell activation in a HLA-DRβ1*0401 transgenic mouse model," Arthritis Res. Ther., 2003, 5(1):R40-8.

Ilan et al., "Oral Administration of OKT3 Monoclonal Antibody to Human Subjects Induces a Dose-Dependent Immunologic Effect in T Cells and Dendritic Cells," J. Clin. Immunol., 2010, 30:167-77.

International Preliminary Report on Patentability in International Application No. PCT/IB2013/001165, dated Dec. 16, 2014, 5 pages.

International Search Report and Written Opinion in International Application No. PCT/IB2013/001165, dated Sep. 24, 2013, 8 pages.

Norman, "Mechanisms of action and overview of OKT3," Ther. Drug Monit., Dec. 1995, 17(6):615-20.

Perry et al., "New Approaches to Prediction of Immune Responses to Therapeutic Proteins during Preclinical Development," Drugs in R&D, 2008, 9(6):385-96.

Tran et al., "Reversal of experimental allergic encephalomyelitis with non-mitogenic, non-depleting anti-CD3 mAb therapy with a preferential effect on Th1 cells that is augmented by IL-4," Intl. Immunol., 2001, 13:1109-20.

Abbs et al., (1994) Sparing of first dose effect of monovalent anti-CD3 antibody used in allograft rejection is associated with diminished release of pro-inflammatory cytokines. Ther Immunol 1(6): 325-31.

Altschul et al., (1990) Basic local alignment search tool. J Mol Biol 215(3): 403-10.

Angal et al., (1993) A single amino acid substitution abolishes the heterogeneity of chimeric mouse/human (IgG4) antibody. Mol Immunol 30(1): 105-8.

Beaucauge and Caruthers (1981) Deoxynucleoside phosphoramidites—A new class of key intermediates for leoxypolynucleotide synthesis. Tetrahedron Letters 22(20): 1859-1862.

Brown et al., (1979) Chemical synthesis and cloning of a tyrosine tRNA gene. Methods Enzymol 68: 109-51.

Brown et al., (1980) Protein antigens of normal and malignant human cells identified by immunoprecipitation with monoclonal antibodies. J Biol Chem 255: 4980-3.

Brown et al., (1981) Structural characterization of human melanoma-associated antigen p97 with monoclonal antibodies. J Immunol 127(2): 539-46.

Bryson et al., (2010) Prediction of immunogenicity of therapeutic proteins: validity of computational tools. BioDrugs 24 (1): 1-8.

Carrillo and Lipman (1988) The Multiple Sequence Alignment Problem in Biology. SIAM J Appl Math 48(5): 1073-1082.

Chaturvedi et al., (1996) Stabilization of triple-stranded oligonucleotide complexes: use of probes containing alternating phosphodiester and stereo-uniform cationic phosphoramidate linkages. Nucleic Acids Res 24(12): 2318-23.

Chothia et al., (1985) Domain association in immunoglobulin molecules. The packing of variable domains. J Mol Biol 186(3): 651-63.

Chothia et al., (1989) Conformations of immunoglobulin hypervariable regions. Nature 342(6252): 877-83.

Clackson et al., (1991) Making antibody fragments using phage display libraries. Nature 352(6336): 624-8.

Colcher et al., (1999) Single-chain antibodies in pancreatic cancer. Ann N Y Acad Sci 880: 263-80.

Foote and Winter (1992) Antibody framework residues affecting the conformation of the hypervariable loops. J Mol Biol 224(2): 487-99.

Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.

Jones et al., (1986) Replacing the complementarity-determining regions in a human antibody with those from a mouse. Nature 321(6069): 522-5.

Jones et al., (2004) The development of a modified human IFN-alpha2b linked to the Fc portion of human IgG1 as a novel potential therapeutic for the treatment of hepatitis C virus infection. J Interferon Cytokine Res 24(9): 560-72.

Jones et al., (2005) Identification and removal of a promiscuous CD4+ T cell epitope from the C1 domain of factor VIII. J Thromb Haemost 3(5): 991-1000.

Kipriyanov et al., (1997) Two amino acid mutations in an anti-human CD3 single chain Fv antibody fragment that affect be yield on bacterial secretion but not the affinity. Protein Eng 10(4): 445-53.

Köhler and Milstein (1975) Continuous cultures of fused cells secreting antibody of predefined specificity. Nature 256 (5517):495-7.

Kozbor and Roder (1983) The production of monoclonal antibodies from human lymphocytes. Immunol Today 4(3): 72-9.

Marks et al., (1991) By-passing immunization. Human antibodies from V-gene libraries displayed on phage. J Mol Biol 222(3): 581-97.

Morrison and Oi (1988) Genetically engineered antibody molecules. Adv Immunol 44: 65-92.

Morrison et al., (1984) Chimeric human antibody molecules: mouse antigen-binding domains with human constant region domains. Proc Natl Acad Sci U S A 81(21): 6851-6855.

Narang et al., (1979) Improved phosphotriester method for the synthesis of gene fragments. Methods Enzymol 68: 90-8.

Niwa et al., (1999) A role for presenilin-1 in nuclear accumulation of Ire1 fragments and induction of the mammalian infolded protein response. Cell 99(7): 691-702.

Novotny and Haber (1985) Structural invariants of antigen binding: comparison of immunoglobulin VL-VH and VL-VL domain dimers. Proc Natl Acad Sci U S A 82(14): 4592-6.

Padlan (1991) A possible procedure for reducing the immunogenicity of antibody variable domains while preserving their ligand-binding properties. Mol Immunol 28(4-5): 489-98.

Peyrottes et al., (1996) Oligodeoxynucleoside phosphoramidates (P-NH2): synthesis and thermal stability of duplexes with DNA and RNA targets. Nucleic Acids Res 24(10): 1841-8.

(56) References Cited

OTHER PUBLICATIONS

Reiter (1996) Antibody engineering of recombinant Fv immunotoxins for improved targeting of cancer: disulfide-stabilized Fv immunotoxins. Clin Cancer Res 2(2): 245-52.
Verhoeyen et al., (1988) Reshaping human antibodies: grafting an antilysozyme activity. Science 239(4847): 1534-6.
Ward et al., (1989) Binding activities of a repertoire of single immunoglobulin variable domains secreted from *Escherichia coli*. Nature 341(6242): 544-6.
Wu and Kabat (1970) An analysis of the sequences of the variable regions of Bence Jones proteins and myeloma light chains and their implications for antibody complementarity. J Exp Med 132(2): 211-50.
Yeh et al., (1976) Cell surface antigens of human melanoma identified by monoclonal antibody. Proc Natl Acad Sci U S A 76(6): 2927-31.
Yeh et al., (1982) A cell-surface antigen which is present in the ganglioside fraction and shared by human melanomas. Int J Cancer 29(3): 269-75.

\* cited by examiner

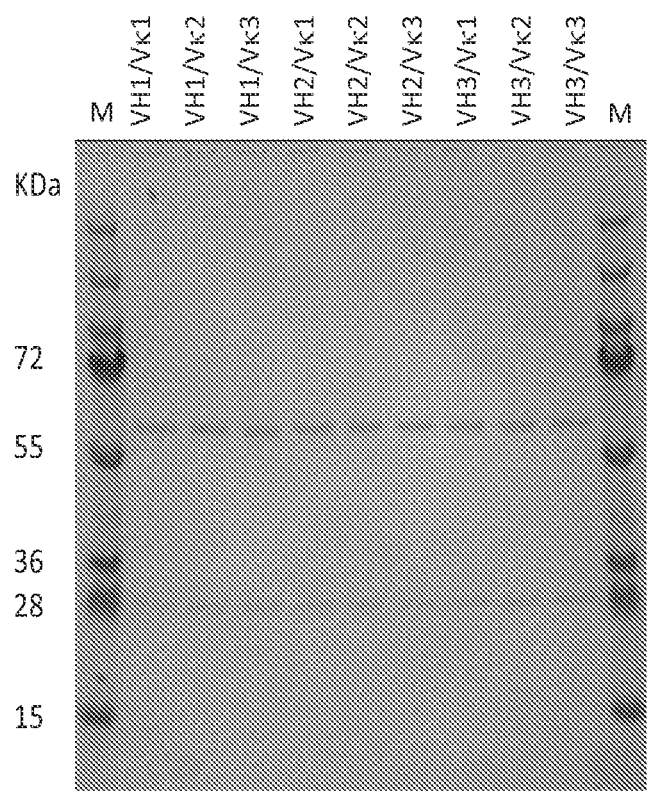

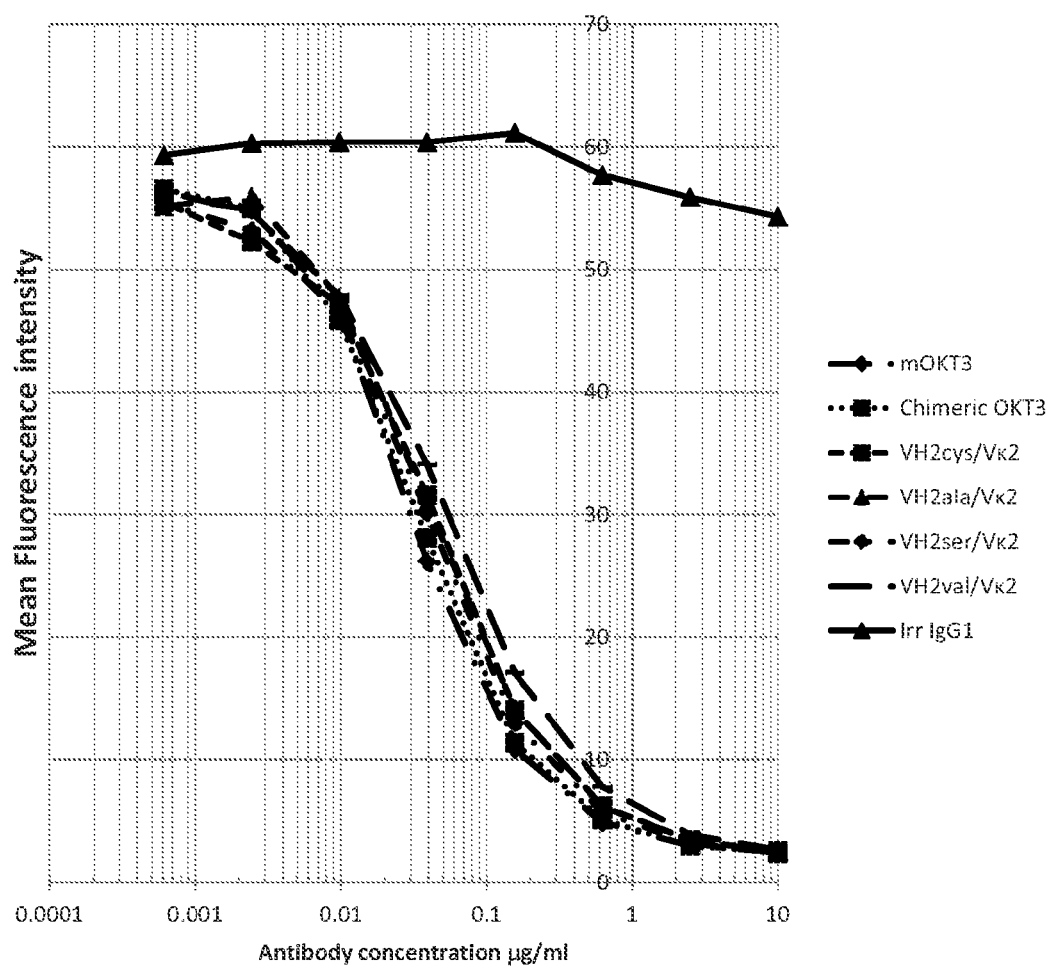

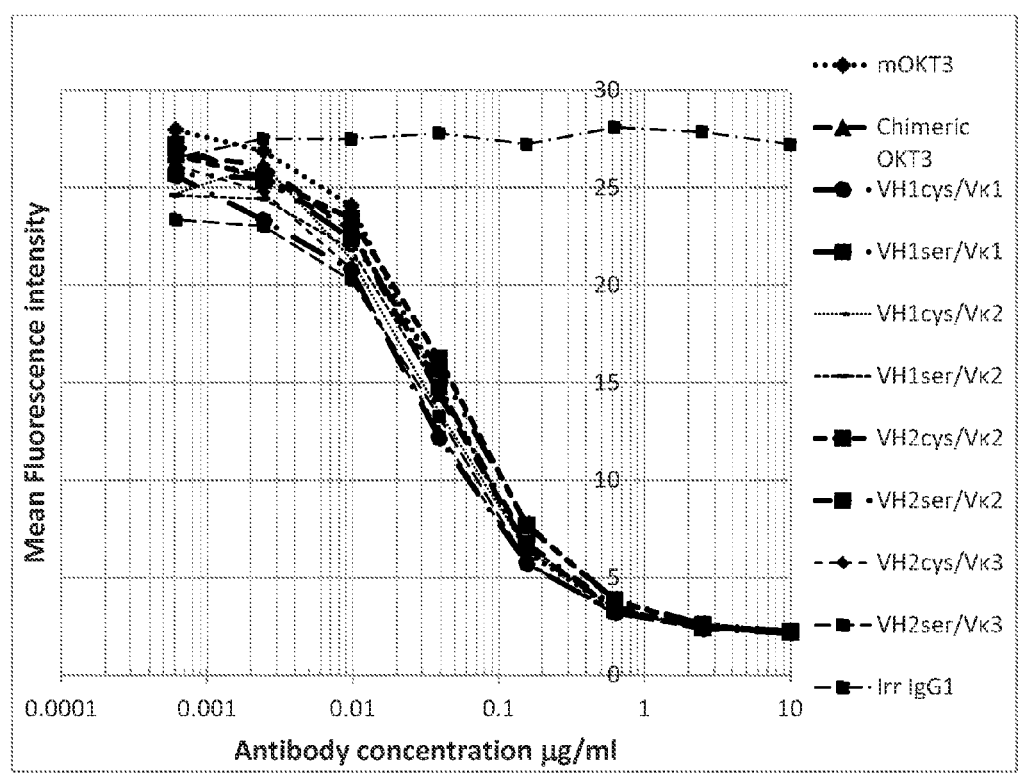

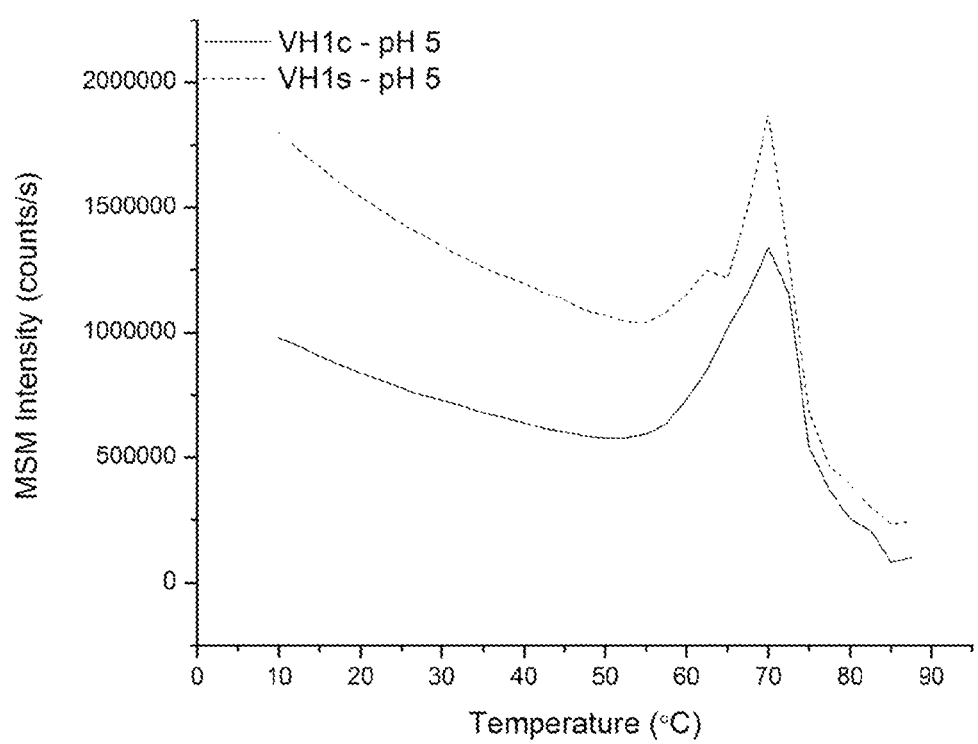

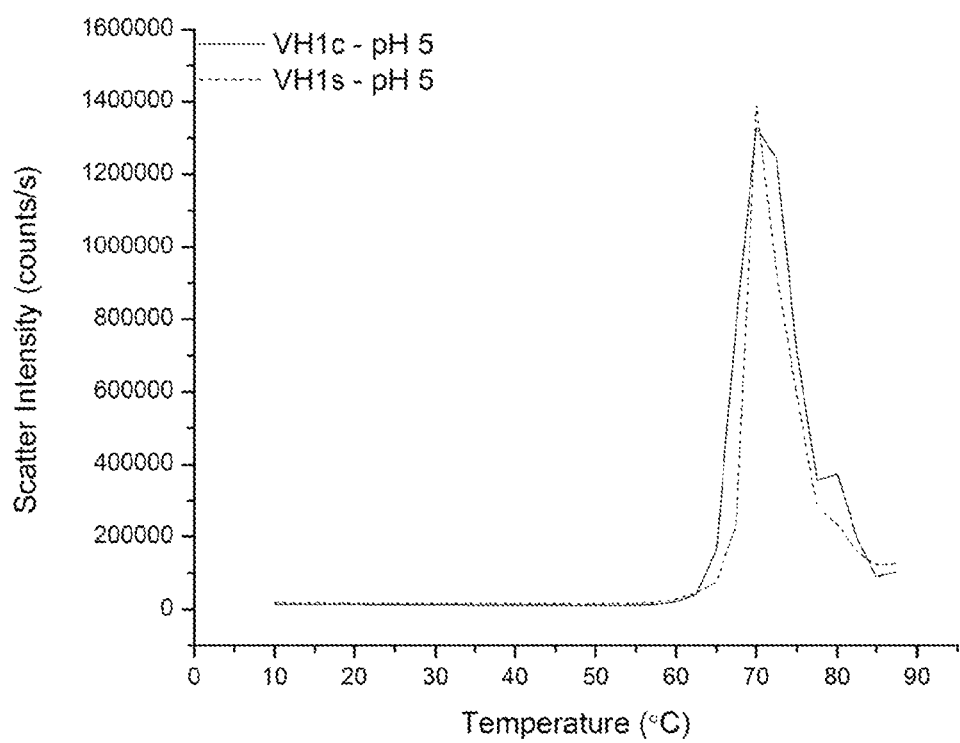

SEQUENCE LISTING

```
<160> NUMBER OF SEQ ID NOS: 48

<210> SEQ ID NO 1
<211> LENGTH: 5
<212> TYPE: PRT
<213> ORGANISM: Artificial
<220> FEATURE:
<223> OTHER INFORMATION: Synthetically generated peptide

<400> SEQUENCE: 1

Arg Tyr Thr Met His
1               5
```

```
<210> SEQ ID NO 2
<211> LENGTH: 17
<212> TYPE: PRT
<213> ORGANISM: Artificial
<220> FEATURE:
<223> OTHER INFORMATION: Synthetically generated peptide

<400> SEQUENCE: 2

Tyr Ile Asn Pro Ser Arg Gly Tyr Thr Asn Tyr Asn Gln Lys Phe Lys
1               5                   10                  15

Asp

<210> SEQ ID NO 3
<211> LENGTH: 10
<212> TYPE: PRT
<213> ORGANISM: Artificial
<220> FEATURE:
<223> OTHER INFORMATION: Synthetically generated peptide

<400> SEQUENCE: 3

Tyr Tyr Asp Asp His Tyr Ser Leu Asp Tyr
1               5                   10

<210> SEQ ID NO 4
<211> LENGTH: 10
<212> TYPE: PRT
<213> ORGANISM: Artificial
<220> FEATURE:
<223> OTHER INFORMATION: Synthetically generated peptide

<400> SEQUENCE: 4

Ser Ala Ser Ser Ser Val Ser Tyr Met Asn
1               5                   10

<210> SEQ ID NO 5
<211> LENGTH: 7
<212> TYPE: PRT
<213> ORGANISM: Artificial
<220> FEATURE:
<223> OTHER INFORMATION: Synthetically generated peptide

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Artificial
<220> FEATURE:
<223> OTHER INFORMATION: Synthetically generated peptide

<400> SEQUENCE: 6

Gln Gln Trp Ser Ser Asn Pro Phe Thr
1               5

<210> SEQ ID NO 7
<211> LENGTH: 119
<212> TYPE: PRT
<213> ORGANISM: Artificial
<220> FEATURE:
<223> OTHER INFORMATION: Synthetically generated protein

<400> SEQUENCE: 7

Gln Val Gln Leu Gln Gln Ser Gly Ala Glu Leu Ala Arg Pro Gly Ala
```

-continued

```
1               5                   10                  15
Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
            50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

<210> SEQ ID NO 8
<211> LENGTH: 106
<212> TYPE: PRT
<213> ORGANISM: Artificial
<220> FEATURE:
<223> OTHER INFORMATION: Synthetically generated protein

<400> SEQUENCE: 8

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
            50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
            85                  90                  95

Phe Gly Ser Gly Thr Lys Leu Glu Ile Asn
            100                 105
```

<210> SEQ ID NO 9
<211> LENGTH: 119
<212> TYPE: PRT
<213> ORGANISM: Artificial
<220> FEATURE:
<223> OTHER INFORMATION: recombinent protein

<400> SEQUENCE: 9

```
Gln Val Gln Leu Val Gln Ser Gly Ser Glu Leu Lys Lys Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Phe
            50                  55                  60

Lys Asp Arg Ala Thr Leu Thr Thr Asp Lys Ser Thr Ser Thr Ala Tyr
65                  70                  75                  80
```

Met Gln Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 10
<211> LENGTH: 106
<212> TYPE: PRT
<213> ORGANISM: Artificial
<220> FEATURE:
<223> OTHER INFORMATION: Synthetically generated protein

<400> SEQUENCE: 10

Gln Ile Val Leu Thr Gln Ser Pro Ala Thr Leu Ser Leu Ser Pro Gly
1               5                   10                  15

Glu Arg Ala Thr Met Ser Cys Ser Ala Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Arg Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gly Gly Thr Lys Val Glu Ile Lys
            100                 105

<210> SEQ ID NO 11
<211> LENGTH: 446
<212> TYPE: PRT
<213> ORGANISM: Artificial
<220> FEATURE:
<223> OTHER INFORMATION: Recombinant protein

<400> SEQUENCE: 11

Gln Val Gln Leu Val Gln Ser Gly Ser Glu Leu Lys Lys Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Ala Thr Leu Thr Thr Asp Lys Ser Thr Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 12
<211> LENGTH: 213
<212> TYPE: PRT
<213> ORGANISM: Artificial
<220> FEATURE:
<223> OTHER INFORMATION: Recombinant protein

<400> SEQUENCE: 12

Gln Ile Val Leu Thr Gln Ser Pro Ala Thr Leu Ser Leu Ser Pro Gly
1               5                   10                  15

Glu Arg Ala Thr Met Ser Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Arg Gly Ser
        50                  55                  60

Gly Ser Gly Thr Asp Tyr Thr Leu Thr Ile Ser Ser Leu Gln Pro Glu
65                  70                  75                  80

```
Asp Phe Ala Thr Tyr Tyr Cys Gln Gln Trp Ser Ser Asn Pro Phe Thr
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 13
<211> LENGTH: 2163
<212> TYPE: DNA
<213> ORGANISM: Artificial
<220> FEATURE:
<223> OTHER INFORMATION: Recombinant DNA

<400> SEQUENCE: 13

```
caggtccagc tggtgcagtc tgggtctgaa ctgaaaaaac ctggggcctc agtgaagatg      60
tcctgcaagg cttctggcta cacctttact aggtacacga tgcactgggt aagacaggcc     120
cctggaaagg gtctggaatg gattggatac attaatccta gccgtggtta ctactaattac    180
aatcagaagt tcaaggacag ggccacattg actacagaca atccaccag cacagcctac      240
atgcaactga gcagcctgag atctgaggac actgcagtct attactgtgc aagatattat     300
gatgatcatt actcccttga ctactggggc caaggcaccc ttgtcacagt ctcctcaggt     360
aagctttctg gggcaggccg ggcctgactt tggctggggg cagggagggg gctaaggtga     420
cgcaggtggc gccagccagg tgcacaccca atgcccatga gcccagacac tggaccctgc     480
atggaccatc gcggatagac aagaaccgag gggcctctgc gccctgggcc agctctgtc      540
ccacaccgcg gtcacatggc accacctctc ttgcagcttc accaagggc ccatccgtct     600
tccccctggc gccctgctcc aggagcacct ccgagagcac agccgccctg gctgcctgg     660
tcaaggacta cttccccgaa ccggtgacgg tgtcgtggaa ctcaggcgcc ctgaccagcg     720
gcgtgcacac cttcccggct gtcctacagt cctcaggact ctactccctc agcagcgtgg    780
tgaccgtgcc ctccagcagc ttgggcacga gacctacac ctgcaatgta gatcacaagc     840
ccagcaacac caaggtggac aagagagttg gtgagaggcc agcacaggga gggagggtgt    900
ctgctggaag ccaggctcag ccctcctgcc tggacgcacc ccggctgtgc agccccagcc    960
cagggcagca aggcaggccc catctgtctc ctcacctgga ggcctctgac cacccccactc   1020
atgctcaggg agagggtctt ctggatttt ccaccaggct ccgggcagcc acaggctgga    1080
tgccccctacc ccaggccctg cgcatacagg ggcaggtgct gcgctcagac ctgccaagag    1140
ccatatccgg gaggaccctg cccctgacct aagcccaccc caaaggccaa actctccact     1200
ccctcagctc agacaccttc tctcctccca gatctgagta actcccaatc ttctctctgc    1260
```

```
agagtccaaa tatggtcccc catgcccacc atgcccaggt aagccaaccc aggcctcgcc    1320
ctccagctca aggcgggaca ggtgcccta g agtagcctgc atccagggac aggccccagc    1380
cgggtgctga cgcatccacc tccatctctt cctcagcacc tgagttcctg ggggga ccat    1440 cagtcttcct gttcccccca aacccaagg acactctcat gatctcccgg accccctgagg    1500 tcacgtgcgt ggtggtggac gtgagccagg aagaccccga ggtccagttc aactggtacg    1560
tggatggcgt ggaggtgcat aatgccaaga caaagccgcg ggaggagcag ttcaacagca    1620
cgtaccgtgt ggtcagcgtc ctcaccgtcc tgcaccagga ctggctgaac ggcaaggagt    1680
acaagtgcaa ggtctccaac aaaggcctcc cgtcctccat cgagaaaacc atctccaaag    1740
ccaaaggtgg gacccacggg gtgcgagggc cacatggaca gaggtcagct cggcccaccc    1800
tctgccctgg gagtgaccgc tgtgccaacc tctgtcccta cagggcagcc ccgagagcca    1860
caggtgtaca ccctgccccc atcccaggag gagatgacca agaaccaggt cagcctgacc    1920
tgcctggtca aaggcttcta ccccagcgac atcgccgtgg agtgggagag caatgggcag    1980
ccggagaaca actacaagac cacgcctccc gtgctggact ccgacggctc cttcttcctc    2040
tacagcaggc taaccgtgga caagagcagg tggcaggagg ggaatgtctt ctcatgctcc    2100
gtgatgcatg aggctctgca caaccactac acacagaaga gcctctccct gtctctgggt    2160
aaa                                                                  2163

<210> SEQ ID NO 14
<211> LENGTH: 1015
<212> TYPE: DNA
<213> ORGANISM: Artificial
<220> FEATURE:
<223> OTHER INFORMATION: Recombinant DNA

<400> SEQUENCE: 14
caaattgttc tcacccagtc tccagcaacc ctgtctctgt ctccagggga gagggccacc      60
atgtcctgca gtgccagctc aagtgtaagt tacatgaact ggtaccagca gaagccaggc     120
aaagccccca aaagatggat ttatgacaca tccaaactgg cttctggagt cccttctagg     180 ttcagggca gtgggtctgg gaccgattac actctcacaa tcagcagcct gcagcctgaa     240
gattttgcca cttattactg ccagcagtgg agtagtaacc cattcacgtt cggcggcggg     300
acaaaggtgg aaataaaacg tgagtagaat ttaaactttg cttcctcagt ggatcccgc     360 aattctaaac tctgaggggg tcggatgacg tggccattct ttgcctaaag cattgagttt     420
actgcaaggt cagaaaagca tgcaaagccc tcagaatggc tgcaaagagc tccaacaaaa     480
caatttagaa cttta ttaag gatagggg aagctaggaa gaaactcaaa acatcaagat     540
tttaaatacg cttcttggtc tccttgctat aattatctgg gataagcatg ctgttttctg     600
tctgtcccta acatgccctg tgattatccg caaacaacac acccaagggc agaactttgt     660
tacttaaaca ccatcctgtt tgcttctttc ctcaggaact gtggctgcac catctgtctt     720
catcttcccg ccatctgatg agcagttgaa atctggaact gcctctgttg tgtgcctgct     780
gaataacttc tatcccagag aggccaaagt acagtggaag gtggataacg ccctccaatc     840
gggtaactcc caggagagtg tcacagagca ggacagcaag gacagcacct acagcctcag     900
cagcaccctg acgctgagca agcagacta cgagaaacac aaagtctacg cctgcgaagt     960
cacccatcag ggcctgagct cgcccgtcac aaagagcttc aacaggggag agtgt        1015

<210> SEQ ID NO 15
```

<211> LENGTH: 449
<212> TYPE: PRT
<213> ORGANISM: Artificial
<220> FEATURE:
<223> OTHER INFORMATION: Recombinant protein

<400> SEQUENCE: 15

```
Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Arg Tyr
            20                  25                  30
Thr Met His Trp Val Lys Gln Arg Pro Gly Gln Gly Leu Glu Trp Ile
        35                  40                  45
Gly Tyr Ile Asn Pro Ser Arg Gly Tyr Thr Asn Tyr Asn Gln Lys Phe
    50                  55                  60
Lys Asp Lys Ala Thr Leu Thr Thr Asp Lys Ser Ser Thr Ala Tyr
65                  70                  75                  80
Met Gln Leu Ser Ser Leu Thr Ser Glu Asp Ser Ala Val Tyr Tyr Cys
            85                  90                  95
Ala Arg Tyr Tyr Asp Asp His Tyr Cys Leu Asp Tyr Trp Gly Gln Gly
            100                 105                 110
Thr Thr Leu Thr Val Ser Ser Ala Lys Thr Thr Ala Pro Ser Val Tyr
        115                 120                 125
Pro Leu Ala Pro Val Cys Gly Asp Thr Thr Gly Ser Ser Val Thr Leu
    130                 135                 140
Gly Cys Leu Val Lys Gly Tyr Phe Pro Glu Pro Val Thr Leu Thr Trp
145                 150                 155                 160
Asn Ser Gly Ser Leu Ser Ser Gly Val His Thr Phe Pro Ala Val Leu
            165                 170                 175
Gln Ser Asp Leu Tyr Thr Leu Ser Ser Val Thr Val Thr Ser Ser
            180                 185                 190
Thr Trp Pro Ser Gln Ser Ile Thr Cys Asn Val Ala His Pro Ala Ser
        195                 200                 205
Ser Thr Lys Val Asp Lys Lys Ile Glu Pro Arg Gly Pro Thr Ile Lys
    210                 215                 220
Pro Cys Pro Pro Cys Lys Cys Pro Ala Pro Asn Leu Leu Gly Gly Pro
225                 230                 235                 240
Ser Val Phe Ile Phe Pro Pro Lys Ile Lys Asp Val Leu Met Ile Ser
            245                 250                 255
Leu Ser Pro Ile Val Thr Cys Val Val Val Asp Val Ser Glu Asp Asp
            260                 265                 270
Pro Asp Val Gln Ile Ser Trp Phe Val Asn Asn Val Glu Val His Thr
        275                 280                 285
Ala Gln Thr Gln Thr His Arg Glu Asp Tyr Asn Ser Thr Leu Arg Val
    290                 295                 300
Val Ser Ala Leu Pro Ile Gln His Gln Asp Trp Met Ser Gly Lys Glu
305                 310                 315                 320
Phe Lys Cys Lys Val Asn Asn Lys Asp Leu Pro Ala Pro Ile Glu Arg
            325                 330                 335
Thr Ile Ser Lys Pro Lys Gly Ser Val Arg Ala Pro Gln Val Tyr Val
            340                 345                 350
Leu Pro Pro Pro Glu Glu Glu Met Thr Lys Lys Gln Val Thr Leu Thr
        355                 360                 365
Cys Met Val Thr Asp Phe Met Pro Glu Asp Ile Tyr Val Glu Trp Thr
    370                 375                 380
```

```
Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val His Glu
            420                 425                 430

Gly Leu His Asn His His Thr Thr Lys Ser Phe Ser Arg Thr Pro Gly
        435                 440                 445

Lys

<210> SEQ ID NO 16
<211> LENGTH: 213
<212> TYPE: PRT
<213> ORGANISM: Artificial
<220> FEATURE:
<223> OTHER INFORMATION: Recombinant protein

<400> SEQUENCE: 16

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 17
<211> LENGTH: 118
<212> TYPE: PRT
<213> ORGANISM: Artificial
<220> FEATURE:
<223> OTHER INFORMATION: Recombinant protein

<400> SEQUENCE: 17

Gln Val Gln Leu Val Gln Ser Gly Ser Glu Leu Lys Lys Pro Gly Ala
1               5                   10                  15
```

Ser Val Lys Val Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser
        115

<210> SEQ ID NO 18
<211> LENGTH: 119
<212> TYPE: PRT
<213> ORGANISM: Artificial
<220> FEATURE:
<223> OTHER INFORMATION: Recombinant protein

<400> SEQUENCE: 18

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Val Thr Ile Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial
<220> FEATURE:
<223> OTHER INFORMATION: Recombinant protein

<400> SEQUENCE: 19

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Val Thr Ile Thr Thr Asp Lys Ser Thr Ser Thr Ala Tyr

```
              65                  70                  75                  80
Met Glu Leu Ser Ser Leu Arg Ser Glu Asp Thr Ala Val Tyr Tyr Cys
                        85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 20
<211> LENGTH: 106
<212> TYPE: PRT
<213> ORGANISM: Artificial
<220> FEATURE:
<223> OTHER INFORMATION: Recombinant protein

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gly Gly Thr Lys Val Glu Ile Lys
            100                 105

<210> SEQ ID NO 21
<211> LENGTH: 30
<212> TYPE: PRT
<213> ORGANISM: Artificial
<220> FEATURE:
<223> OTHER INFORMATION: Synthetically generated peptide

<400> SEQUENCE: 21

Gln Val Gln Leu Val Gln Ser Gly Ser Glu Leu Lys Lys Pro Gly Ala
1               5                   10                  15

Ser Val Lys Met Ser Cys Lys Ala Ser Gly Tyr Thr Phe Thr
            20                  25                  30

<210> SEQ ID NO 22
<211> LENGTH: 14
<212> TYPE: PRT
<213> ORGANISM: Artificial
<220> FEATURE:
<223> OTHER INFORMATION: Synthetically generated peptide

<400> SEQUENCE: 22

Trp Val Arg Gln Ala Pro Gly Lys Gly Leu Glu Trp Ile Gly
1               5                   10

<210> SEQ ID NO 23
<211> LENGTH: 32
<212> TYPE: PRT
<213> ORGANISM: Artificial
<220> FEATURE:
<223> OTHER INFORMATION: Synthetically generated peptide
```

-continued

```
<400> SEQUENCE: 23

Arg Ala Thr Leu Thr Thr Asp Lys Ser Thr Ser Thr Ala Tyr Met Gln
1               5                   10                  15

Leu Ser Ser Leu Arg Ser Glu Asp Thr Ala Val Tyr Tyr Cys Ala Arg
            20                  25                  30

<210> SEQ ID NO 24
<211> LENGTH: 11
<212> TYPE: PRT
<213> ORGANISM: Artificial
<220> FEATURE:
<223> OTHER INFORMATION: Synthetically generated peptide

<400> SEQUENCE: 24

Trp Gly Gln Gly Thr Leu Val Thr Val Ser Ser
1               5                   10

<210> SEQ ID NO 25
<211> LENGTH: 23
<212> TYPE: PRT
<213> ORGANISM: Artificial
<220> FEATURE:
<223> OTHER INFORMATION: Synthetically generated peptide

<400> SEQUENCE: 25

Gln Ile Val Leu Thr Gln Ser Pro Ala Thr Leu Ser Leu Ser Pro Gly
1               5                   10                  15

Glu Arg Ala Thr Met Ser Cys
            20

<210> SEQ ID NO 26
<211> LENGTH: 15
<212> TYPE: PRT
<213> ORGANISM: Artificial
<220> FEATURE:
<223> OTHER INFORMATION: Synthetically generated peptide

<400> SEQUENCE: 26

Trp Tyr Gln Gln Lys Pro Gly Lys Ala Pro Lys Arg Trp Ile Tyr
1               5                   10                  15

<210> SEQ ID NO 27
<211> LENGTH: 32
<212> TYPE: PRT
<213> ORGANISM: Artificial
<220> FEATURE:
<223> OTHER INFORMATION: Synthetically generated peptide

<400> SEQUENCE: 27

Gly Val Pro Ser Arg Phe Arg Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 28
<211> LENGTH: 10
<212> TYPE: PRT
<213> ORGANISM: Artificial
<220> FEATURE:
<223> OTHER INFORMATION: Synthetically generated peptide

<400> SEQUENCE: 28

Phe Gly Gly Gly Thr Lys Val Glu Ile Lys
1               5                   10
```

```
<210> SEQ ID NO 29
<211> LENGTH: 30
<212> TYPE: PRT
<213> ORGANISM: Artificial
<220> FEATURE:
<223> OTHER INFORMATION: Synthetically generated peptide

<400> SEQUENCE: 29

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 30
<211> LENGTH: 14
<212> TYPE: PRT
<213> ORGANISM: Artificial
<220> FEATURE:
<223> OTHER INFORMATION: Synthetically generated peptide

<400> SEQUENCE: 30

Trp Val Arg Gln Ala Pro Gly Lys Gly Leu Glu Trp Ile Gly
1               5                   10

<210> SEQ ID NO 31
<211> LENGTH: 32
<212> TYPE: PRT
<213> ORGANISM: Artificial
<220> FEATURE:
<223> OTHER INFORMATION: Synthetically generated peptide

<400> SEQUENCE: 31

Arg Ala Thr Ile Thr Thr Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 32
<211> LENGTH: 11
<212> TYPE: PRT
<213> ORGANISM: Artificial
<220> FEATURE:
<223> OTHER INFORMATION: Synthetically generated peptide

<400> SEQUENCE: 32

Trp Gly Gln Gly Thr Leu Val Thr Val Ser Ser
1               5                   10

<210> SEQ ID NO 33
<211> LENGTH: 23
<212> TYPE: PRT
<213> ORGANISM: Artificial
<220> FEATURE:
<223> OTHER INFORMATION: Synthetically generated peptide

<400> SEQUENCE: 33

Gln Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 34
<211> LENGTH: 15
<212> TYPE: PRT
<213> ORGANISM: Artificial
```

```
<220> FEATURE:
<223> OTHER INFORMATION: Synthetically generated peptide

<400> SEQUENCE: 34

Trp Tyr Gln Gln Lys Pro Gly Lys Ala Pro Lys Arg Trp Ile Tyr
1               5                   10                  15

<210> SEQ ID NO 35
<211> LENGTH: 32
<212> TYPE: PRT
<213> ORGANISM: Artificial
<220> FEATURE:
<223> OTHER INFORMATION: Synthetically generated peptide

<400> SEQUENCE: 35

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 36
<211> LENGTH: 10
<212> TYPE: PRT
<213> ORGANISM: Artificial
<220> FEATURE:
<223> OTHER INFORMATION: Synthetically Generated Peptide

<400> SEQUENCE: 36

Phe Gly Gly Gly Thr Lys Val Glu Ile Lys
1               5                   10

<210> SEQ ID NO 37
<211> LENGTH: 30
<212> TYPE: PRT
<213> ORGANISM: Artificial
<220> FEATURE:
<223> OTHER INFORMATION: Synthetically generated peptide

<400> SEQUENCE: 37

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 38
<211> LENGTH: 14
<212> TYPE: PRT
<213> ORGANISM: Artificial
<220> FEATURE:
<223> OTHER INFORMATION: Synthetically generated peptide

<400> SEQUENCE: 38

Trp Val Arg Gln Ala Pro Gly Lys Gly Leu Glu Trp Ile Gly
1               5                   10

<210> SEQ ID NO 39
<211> LENGTH: 32
<212> TYPE: PRT
<213> ORGANISM: Artificial
<220> FEATURE:
<223> OTHER INFORMATION: Synthetically generated peptide

<400> SEQUENCE: 39

Arg Val Thr Ile Thr Thr Asp Lys Ser Thr Ser Thr Ala Tyr Met Glu
1               5                   10                  15
```

```
Leu Ser Ser Leu Arg Ser Glu Asp Thr Ala Val Tyr Tyr Cys Ala Arg
            20                  25                  30

<210> SEQ ID NO 40
<211> LENGTH: 11
<212> TYPE: PRT
<213> ORGANISM: Artificial
<220> FEATURE:
<223> OTHER INFORMATION: Synthetically generated peptide

<400> SEQUENCE: 40

Trp Gly Gln Gly Thr Leu Val Thr Val Ser Ser
1               5                   10

<210> SEQ ID NO 41
<211> LENGTH: 23
<212> TYPE: PRT
<213> ORGANISM: Artificial
<220> FEATURE:
<223> OTHER INFORMATION: Synthetically generated peptide

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 42
<211> LENGTH: 15
<212> TYPE: PRT
<213> ORGANISM: Artificial
<220> FEATURE:
<223> OTHER INFORMATION: Synthetically generated peptide

<400> SEQUENCE: 42

Trp Tyr Gln Gln Lys Pro Gly Lys Ala Pro Lys Arg Trp Ile Tyr
1               5                   10                  15

<210> SEQ ID NO 43
<211> LENGTH: 32
<212> TYPE: PRT
<213> ORGANISM: Artificial
<220> FEATURE:
<223> OTHER INFORMATION: Synthetically generated peptide

<400> SEQUENCE: 43

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 44
<211> LENGTH: 10
<212> TYPE: PRT
<213> ORGANISM: Artificial
<220> FEATURE:
<223> OTHER INFORMATION: Synthetically generated peptide

<400> SEQUENCE: 44

Phe Gly Gly Gly Thr Lys Val Glu Ile Lys
1               5                   10

<210> SEQ ID NO 45
<211> LENGTH: 19
<212> TYPE: PRT
<213> ORGANISM: Artificial
```

```
<220> FEATURE:
<223> OTHER INFORMATION: Synthetically generated peptide

<400> SEQUENCE: 45

Met Gly Trp Ser Leu Ile Leu Leu Phe Leu Val Ala Val Ala Thr Arg
1               5                   10                  15

Val His Ser

<210> SEQ ID NO 46
<211> LENGTH: 20
<212> TYPE: PRT
<213> ORGANISM: Artificial
<220> FEATURE:
<223> OTHER INFORMATION: Synthetically generated peptide

<400> SEQUENCE: 46

Met Arg Val Pro Ala Gln Leu Leu Gly Leu Leu Leu Leu Trp Leu Pro
1               5                   10                  15

Gly Ala Arg Cys
            20

<210> SEQ ID NO 47
<211> LENGTH: 119
<212> TYPE: PRT
<213> ORGANISM: Artificial
<220> FEATURE:
<223> OTHER INFORMATION: Synthetically generated protein

<400> SEQUENCE: 47

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 48
<211> LENGTH: 107
<212> TYPE: PRT
<213> ORGANISM: Artificial
<220> FEATURE:
<223> OTHER INFORMATION: Synthetically generated protein

<400> SEQUENCE: 48

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45
```

```
Asp Thr Ser Lys Leu Ala Ser Gly Val Pro Ala His Phe Arg Gly Ser
    50              55                  60

Gly Ser Gly Thr Ser Tyr Ser Leu Thr Ile Ser Gly Met Glu Ala Glu
65              70                  75                      80

Asp Ala Ala Thr Tyr Tyr Cys Gln Gln Trp Ser Ser Asn Pro Phe Thr
                85              90                  95

Phe Gly Ser Gly Thr Lys Leu Glu Ile Asn Arg
            100             105
```

HUMANIZED ANTIBODIES TO CLUSTER OF DIFFERENTIATION 3 (CD3)

CLAIM OF PRIORITY

The present application claims the benefit of U.S. Provisional Application Ser. No. 61/659,717, filed on Jun. 14, 2012. The entire contents of the foregoing are incorporated herein by reference.

FIELD OF THE INVENTION

The present invention relates to humanized monoclonal antibodies binding specifically to human CD3 (Cluster of Differentiation 3), and fragments thereof, optionally comprising at least the variable region, said variable region comprising specific framework mutations and specific CDRs. The present invention also discloses compositions and methods for producing and using the disclosed antibodies.

BACKGROUND OF THE INVENTION

Immunotherapy strategies involving antibody-induced signaling through antigen-specific T-cell receptors (TCR) have been shown to ameliorate autoimmune and inflammatory diseases, likely by regulating the immune response to self-antigens. CD3 (Cluster of Differentiation 3) is an example of such a receptor. Injected anti-CD3 monoclonal antibody (mAb) therapy in particular has been shown to be efficacious in preventing and reversing the onset of diabetes in NOD mice (Belghith et al, Nat Med 9: 1202-8, 2003) and in treating subjects with Type 1 diabetes (Herold et al, N Engl J Med 346: 1692-82, 2002). Anti-CD3 antibodies also reverse experimental allergic encephalomyelitis (EAE) in Lewis rats with a suppressive effect on T-helper type 1 (Th1) mediated immunity (Tran et al, Intl Immunol 13: 1109-20, 2001). Orthoclone OKT3™ (muromonab-CD3; Ortho Biotech Products, Bridgewater, N.J.) is a murine anti-CD3 IgG2a mAb, approved for intravenous injection for the treatment of graft rejection after transplantation (Chatenoud, Nat Rev Immunol 3: 123-32, 2003). After injection of Orthoclone OKT3™, CD3+ T cells are removed from circulation, what has been effective in reversing corticosteroid-resistant acute graft rejection in renal, liver, and cardiac transplant recipients. Humanized mAbs specific to CD3 were developed, also having reduced binding to the Fcγ receptors. These humanized antibodies include otelixizumab, teplizumab, and visilizumab.

U.S. Pat. No. 7,883,703 (Weiner et al) discloses that anti-CD3 antibodies are also useful for the treatment of autoimmune diseases when administered orally or mucosally. The success of such oral or mucosal administration involves activation of regulatory T cells (Tregs) in the mucosal immune system, which in turn leads to an amelioration or down-regulation of the undesired immune system effects, hence ameliorating or at least reducing the pathology of autoimmune and inflammatory diseases. Among the advantages of the oral or mucosal route over the systemic route of administration of anti-CD3 mAb is the ability to avoid the serious adverse events (AEs) and generalized immune-suppression associated with systemic administration of anti-CD3 mAb.

SUMMARY OF THE INVENTION

There is an unmet need for providing improved mAbs and antibody fragments to CD3, which are not immunogenic, suitable for oral or mucosal administration, have improved pharmaceutical stability, and have biological activity.

With the aim of producing improved humanized mAbs to the protein CD3, it was surprisingly found that a combination of specific mutations in the variable (V) framework regions (FRs), together with specific complementarity-determining regions (CDR) sequences, result in humanized mAbs having improved properties, in particular biological activity and pharmaceutical stability. Such combinations of mutations and CDRs were not previously disclosed, suggested, or expected. Thus improved humanized mAbs to CD3 are provided as well as pharmaceutical compositions comprising them and methods for their use in treating diseases susceptible to amelioration through binding to CD3, wherein "treating" may also optionally comprise preventing.

The present invention provides, according to at least some embodiments, a mAb to CD3 or an antibody fragment thereof comprising at least the V regions, wherein the antibody or antibody fragment comprises the six CDRs set forth in SEQ ID NOs: 1-6 and a humanized FR comprising specific point mutations which render the mAb more pharmaceutically stable and biologically active.

According to some embodiments, the mAb comprises a human constant (C) region.

According to some embodiments, the heavy (H) chain C region is selected from the group consisting of IgG1, IgG2, IgG3, IgG4, IgA, and IgM.

According to some embodiments, the mAb comprises a human IgG4 C region comprising a Ser241Pro mutation.

According to some embodiments, the humanized FR comprises the mutations: Q5V, A9S, A12K, R13K, K38R, R40A, Q43K, K66R, S75T, T83R, S87T, T108L and L109V relative to the sequence of the H chain V region (VH) set forth in SEQ ID NO: 7.

According to some embodiments, the humanized FR comprises the mutations: I10T, M11L, A13L, K18R, V19A, T22S, S40P, T42K, S43A, A60S, H61R, S70D, S72T, G77S, M78L, E79Q, A80P, A83F, S100G, L104V and N107K relative to the sequence of the light (L) kappa (κ) chain V region (Vκ) set forth in SEQ ID NO: 8.

According to some embodiments, the humanized FR comprises the mutations: Q5V, A9S, A12K, R13K, M20V, K38R, R40A, Q43K, K66R, L69I, S75T, Q81E, T83R, S87T, T108L and L109V relative to the sequence of the VH region set forth in SEQ ID NO: 7; as well as the mutations: Q1E, I10T, M11L, A13L, K18R, V19A, M21L, T22S, S40P, T42K, S43A, A60S, H61R, R63S, S70D, S72T, G77S, M78L, E79Q, A80P, A83F, S100G, L104V and N107K relative to the sequence of the Vκ region set forth in SEQ ID NO: 8.

According to some embodiments, the mAb or it fragment comprises a VH chain set forth in SEQ ID NO: 9.

According to other embodiments, the mAb or its fragment comprises a Vκ chain set forth in SEQ ID NO: 10.

According to some embodiments, the mAb or its fragment comprises a VH chain set forth in SEQ ID NO: 9 and a Vκ chain set forth in SEQ ID NO: 10.

According to some embodiments, the mAb or its fragment comprises a full-length H chain according to SEQ ID NO: 11 and a full-length L chain according to SEQ ID NO: 12.

According to some embodiments, the mAb comprises a H chain sequence having at least 95% identity to SEQ ID NO: 9 and a κ chain sequence having at least 95% identity to SEQ ID NO: 10.

According to some embodiments, the mAb comprises VH and Vκ chain sequences having at least 96%, 97%, 98% or 99% identity to SEQ ID NOs: 9 and 10 respectively. Each possibility represents a separate embodiment of the invention.

According to some embodiments, the VH chain is encoded by a polynucleotide sequence comprising a sequence set forth in SEQ ID NO: 13.

According to some embodiments, the Vκ chain is encoded by a polynucleotide sequence comprising a sequence set forth in SEQ ID NO: 14.

It is obvious to those skilled in the art that the redundancy of DNA codons means that each amino acid is encoded by one or more codons, such that there can be at least 30% variability in DNA sequences encoding the identical polypeptide.

It is obvious to those skilled in the art that the DNA sequences of SEQ ID NO: 13 and 14, which contain introns, still encode the VH and VL chains in the same way that SEQ ID NO: 13 and 14 without introns also encode VH and VL.

Included in the scope of the present invention also are antibody fragments comprising the specific mutations to the FR and the six CDR sequences of SEQ ID NOs: 1-6.

An antibody fragment according to the present invention comprises at least the V region of the antibody. In some embodiments, the antibody fragment is selected from the group consisting of: Fab, Fab', F(ab')$_2$, scFv, or dsFv antibody.

The present invention provides, according to another aspect, a pharmaceutical composition comprising as an active ingredient a mAb to CD3 as described above, and optionally comprising excipient or carrier.

In some embodiments, the pharmaceutical compositions further comprise pharmaceutically acceptable excipients and/or carriers. In some embodiments, the pharmaceutical compositions further comprise additional active or inactive ingredients.

According to some embodiments, the pharmaceutical composition is formulated for an administration route selected from the group consisting of: oral, mucosal, nasal, intranasal, pulmonary, sublingual, buccal, rectal, or vaginal.

According to some embodiments, a pharmaceutical composition suitable for oral administration is provided wherein the composition is in a form selected from the group consisting of: a liquid oral dosage form and a solid oral dosage form, e.g., tablets, capsules, caplets, powders, pellets, granules, powder in a sachet, enteric-coated capsules, enteric-coated tablets, enteric coated beads, encapsulated powders, encapsulated pellets, encapsulated granules, and enteric-coated soft gel capsules.

According to some embodiments, the oral dosage form is a controlled release formulation.

The present invention provides, according to yet another aspect, polynucleotide sequences encoding polypeptide sequences of mAbs or a fragment, chain or domain thereof, directed against CD3.

According to some embodiments a polynucleotide sequence comprising the 85%, 90% or 95% identity with SEQ ID NO: 13, encoding a mAb H chain as in SEQ ID NO: 11, is provided.

According to some embodiments a polynucleotide sequence comprising the sequence set forth in SEQ ID NO: 13, or a sequence having at least 90% identity with SEQ ID NO: 13, encoding a mAb H chain as in SEQ ID NO: 11, is provided.

According to some embodiments a polynucleotide sequence comprising the sequence set forth in SEQ ID NO: 14, or a sequence having at least 70%, 75%, 80%, 85%, 90% or 95% identity with SEQ ID NO: 14, encoding a mAb L (κ) chain as in SEQ ID NO: 12, is provided.

According to some embodiments a polynucleotide sequence comprising the sequence set forth in SEQ ID NO: 14, or a sequence having at least 90% identity with SEQ ID NO: 14, encoding a mAb L (κ) chain as in SEQ ID NO: 12, is provided.

According to some embodiments a polynucleotide sequence is provided comprising at least one sequence set forth in SEQ ID NO:13 or SEQ ID NO: 14, or a sequence having at least 70%, 75%, 80%, 85%, 90% or 95% identity to SEQ ID NO:13 or SEQ ID NO: 14.

Expression vectors containing at least one polynucleotide sequence encoding a polypeptide of a mAb or fragment thereof as described herein are also included in the scope of the present invention, as well as host cells and transgenic animals comprising these expression vectors or polynucleotide sequences.

Another aspect relates to recombinant host cells comprising an expression vector encoding a mAb or a fragment thereof as described herein.

According to some embodiments, the host is a hybridoma cell line expressing a mAb or a fragment, chain or domain thereof.

Use of a mAb according to the invention or a fragment thereof comprising at least the V regions for treatment, e.g., of a condition or disease described herein, or for preparation of a medicament, also are within the scope of the present invention.

Another aspect provides a pharmaceutical composition comprising a mAb according to the invention or a fragment thereof comprising at least the V regions for treating a disease or disorder susceptible to amelioration by binding to CD3.

According to some embodiments, the pharmaceutical composition further comprises excipient, diluent or carrier.

According to some embodiments, the pharmaceutical composition is formulated for oral or mucosal administration.

According to yet another aspect the invention provides a method for treating a disease or disorder susceptible to amelioration by binding to CD3, comprising administering to a subject in need thereof a pharmaceutical composition comprising a mAb or a fragment thereof comprising at least the variable regions, according to the invention.

According to some embodiments, the disease is an autoimmune or an inflammatory disease.

According to a specific embodiment the disease is hepatitis of any etiology.

Any route of administration can be used for treatment according to the invention, including but not limited to an administration route selected from the group consisting of: oral, mucosal, nasal, intranasal, pulmonary, sublingual, buccal, rectal, or vaginal.

According to some embodiments, the administration is through the oral or mucosal routes.

According to other embodiments, the administration route is selected from the group consisting of: nasal, intranasal, pulmonary, sublingual, buccal, rectal, or vaginal.

The pharmaceutical composition according to the present invention may be administered as a stand-alone treatment or in addition to a treatment with any other therapeutic agent. The pharmaceutical composition according to the present invention may be administered together with the other agent or separately.

Methods for producing mAbs to CD3 or fragments thereof comprising at least the V regions are also within the scope of the present invention.

A mAb according to the present invention or a fragment thereof may be produced by any suitable method known in the art. This includes isolation from recombinant host cells, hybridoma cells or other biological systems, or synthetic production.

In some embodiments, a mAb according to the invention is produced by a method comprising the steps of:

(a) producing a preparation of an antigen related to human CD3, or a fragment, or a cell containing CD3 or a fragment, or a fusion protein thereof;

(b) immunizing a rodent, e.g., a mouse, with the antigen, or a fragment, or a fusion protein thereof, or a cell containing said antigen;

(c) detecting specifically binding or blocking Abs in the serum of the mice;

(d) producing hybridomas between lymph node cells from the mice and myeloma cells to produce Abs; and (e) screening hybridomas with an antigen-specific binding assay.

In some embodiments, an antigen used to produce antibodies (Abs) is human, or from a subhuman primate species.

In some embodiments, the antigen used to produce Abs is a primary cell or cell line expressing endogenous or recombinant full length antigen or an antigenic fragment of the antigen, or a fusion protein of all or part of the antigen and another protein, or the antigen is part of a virus-like particle.

In some embodiments, the antigen used to produce Abs is on the surface of cells.

As an alternative to steps b), c) and d), an antibody, or fragment thereof comprising at least the V chains, can be obtained by selecting antibody sequences by phage display on the antigen of step a).

Essentially all of the uses known or envisioned in the prior art for anti-CD3 Abs can be accomplished with the Abs of the present invention which are shown to possess improved biological and pharmaceutical properties that are improved over previously known Abs. These uses include prophylactic (preventive) and therapeutic applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and not intended to be limiting. Other features and advantages of the invention will be apparent from the following detailed description, and from the claims.

BRIEF DESCRIPTION OF THE DRAWINGS

FIG. 3. SDS-PAGE profile of protein A-purified humanized mAbs. mAb (0.5 μg) was loaded on a NuPage 4-12% Bis-Tris gel, run at 200 V for 30 min, and stained with Coomassie Blue. Molecular marker (M) is Fermentas PageRuler™ Plus.

FIGS. 4A and 4B. Quantitative binding competition of humanized mAb variants with labeled OKT to Jurkat cells. A dilution series (10 to 0.0006 μg/mL) of each of the antibodies: unlabeled CD3 monoclonal antibody (OKT) (eBiosciences™ Cat. No. 16-0037-85), Chimeric anti-CD3 mAb, negative control IgG1 ("Irr IgG1"), or different mutants of VH2/VK2 humanized mAbs, was mixed with a constant ED50 concentration (0.02 μg/mL) of OKT3-PE and incubated on ice for 1 hr with 3×10⁵ Jurkat cells per dilution in FACS buffer. Cells then were washed and resuspended in 300 μL FACS buffer and analyzed on a Becton Dickinson FACScalibur™. The tested humanized mAbs are (A) VH2/VK2 variants mAbs with Cys (VH2/VK2), Ala, Ser or Val residue at position 100A; and (B) variants having different combinations of VH and VK chains and Cys or Ser residue at position 100A.

FIGS. 9A-9C. Spectroscopic analyses of mAbs at pH5. Mean spectral mass peak position (A) and intensity (B) obtained from intrinsic fluorescence experiments and from light scattering (C) were quantified at pH5 as a function of temperature from 10 to 87.5° C. Data are shown for VH1cys/Vκ1 (solid lines) and VH1ser/Vκ1 (dotted lines).

DETAILED DESCRIPTION OF THE INVENTION

Figure 1:
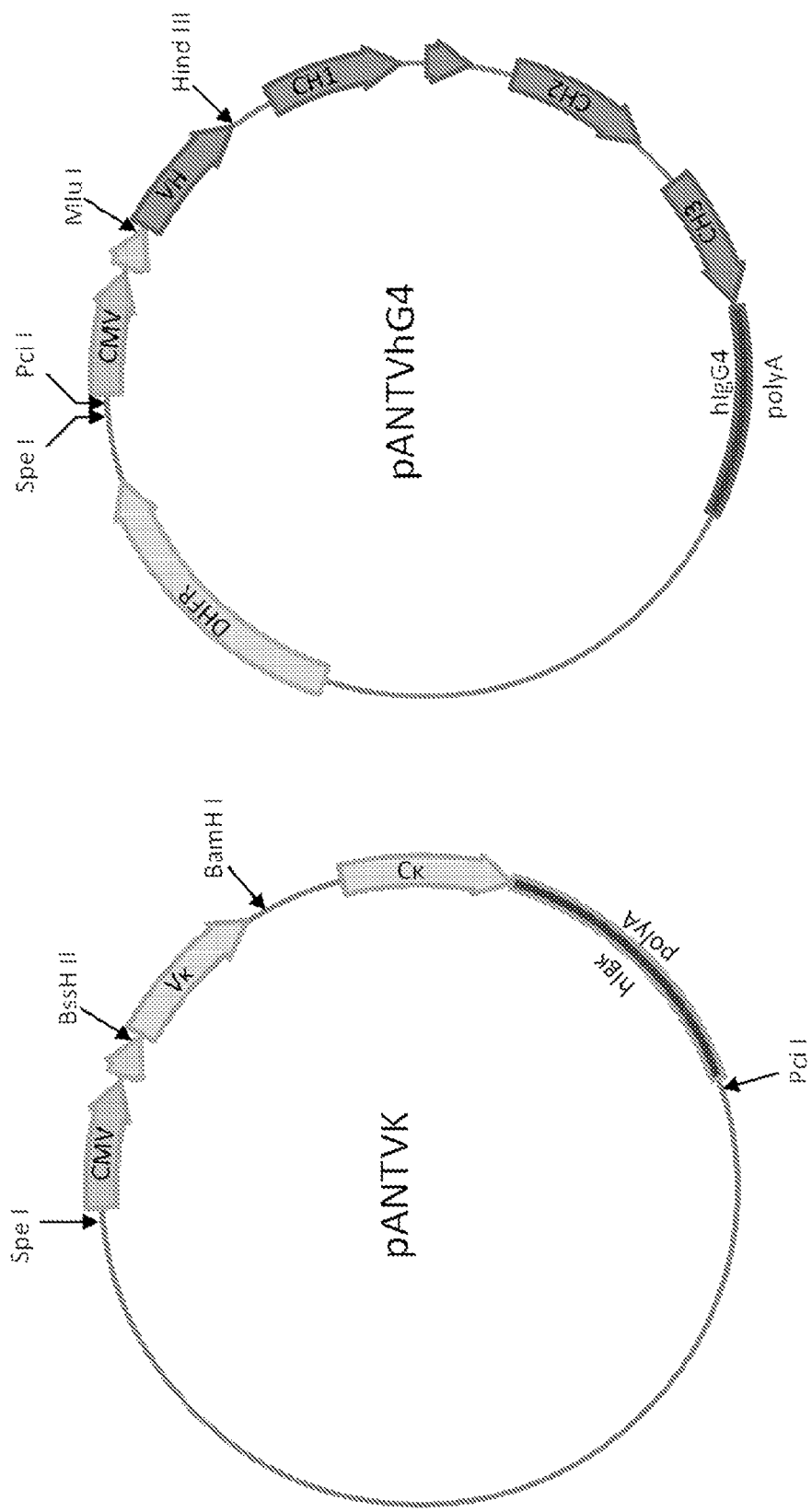
FIG. 1. Schematic diagrams of pANT vector encoding chimeric antibody Vκ (Left) and VH (right) sequences. Both vectors contain genomic DNA fragments incorporating introns and poly-A sequences, and an EBV OriP for enhanced transient expression in HEK/EBNA cells.

The present invention provides, in at least some embodiments, novel mAbs to CD3, and fragments thereof, and methods for use thereof and compositions thereof, or treatment of diseases that are susceptible to amelioration by binding CD3, for example by using oral or mucosal delivery, wherein treatment also optionally comprises prevention of such diseases.

The present invention is directed to specific mAb variants having enhanced biological activity and pharmaceutical stability. The structure of the mAb is based on unique juxtaposition of composite humanized FRs, a single point mutation in the V domain of H chain CDR number 3 (CDR3), and several specific mutations to the VH and Vκ region FRs. This novel mAb maintains high and specific binding capacity to the CD3 T-cell-surface molecule, shows unexpectedly improve pharmaceutical stability relative to both OKT3 and to another humanized anti-CD3 MAb with the same CDRs and closely related FRs, eliminate immunogenicity with newly designed FRs, and provide for an unexpectedly increased biological signal for stimulating activity toward T cells, and as a consequence should enhance the clinical efficacy profile of the mAb. Unique structural features also have utility for the oral route of administration.

The antibodies of the present invention, in at least some embodiments, comprise the CDRs of the OKT3 mAb that also contain a serine (Ser) instead of a cysteine (Cys) residue at position 100A of the heavy (H) chain (according to the Kabat numbering system, several positions after residue 100 are numbered 100A, 100B, etc.) and a point mutation that was described for a single-chain Fv molecule (Kipriyanov et al., Protein Engineering 10: 445-53, 1997).

The mAbs of the present invention thus preserve the precise binding specificity of the OKT3 mAb which has clinically proven activity when administered parenterally and orally to subjects with inflammatory and other diseases.

According to at least some embodiments, the novel mAbs are fully humanized and de-immunized, have sequence-specific FRs, and feature a mutation at amino acid residue 100A (Kabat numbering system), in which the native Cys is changed to Ser. That is, the mAb features the point mutation Cys100ASer in the VH-CDR3 domain of a fully humanized anti-CD3 mAb. This humanized mAb is derived from OKT3 VH (VH chain) and Vκ(VL chain) regions according to the published sequences of the two mAb chains Mus musculus OKT3 L chain (EMBL accession A22259.1 GI:641464) and OKT3 H chain (EMBL accession A22261.1 GI:21727144), or Muromonab in DrugBank accession number DB00075 (BIOD00005, BTD00005, www.drugbank.ca/drugs/DB00075).

Without wishing to be limited, the humanization and de-immunization were performed by constructing a Chimeric mAb against CD3 comprised of murine mAb (OKT3) VH and VL regions, and human IgG4 H chain and κ chain C regions. The IgG4 CH region also contains a mutation (Ser241Pro) that is known to abolish the formation of IgG4 half-antibodies and chain exchange (Angal et al, Molec Immunol 30: 105-8, 1993). The Chimeric mAb is humanized by changing the VH and VL region FRs, as described below.

Among the CDRs, VH-CDR3 contains an unpaired Cys residue (Cys100A), meaning that the full IgG molecule contains an odd number of Cys residues, such that Cys100A cannot form its own natural intramolecular disulfide bond as do all other Cys residues in the IgG molecule. Such an unpaired Cys residue is very unusual among published mAb sequences in that only ~0.1% of CDR sequences contain an unpaired Cys residue. MAbs ordinarily have an even number of Cys residues, which form natural intra-IgG disulfide bonds. The unpaired Cys residue could enable the mAb to form an intermolecular disulfide bond with another molecule (in particular, another IgG, e.g., in a preparation of purified IgG mAb for therapeutic use) or an intramolecular disulfide bond (disulfide "shuffling" or exchange with another Cys residue that would change the secondary and tertiary structure of the mAb, hence diminish its activity) during the time of storage of a preparation of purified IgG, which would be a source of inappropriate folding or molecular assembly and instability and undesirable pharmaceutically in a protein-based product from the point of view of clinical and regulatory issues. Thus, mutating Cys100A in VH CDR3 was performed to potentially reduce pharmaceutical problems associated with an unpaired Cys residue.

However, mutating an amino acid residue in a CDR runs the risk of reducing the potency of the mAb in terms of binding and biological activity, and is therefore a non-obvious mutation to make. Furthermore, even if a point mutation such as Cys100A in the context of the FRs of OKT3 mAb or in the context of a fragment of a full mAb is acceptable for binding to CD3+ cells and for enhancing the stability of the resulting mAb, there should be no a-priori expectation that the same Cys100A mutation in the context of humanized FRs would be acceptable for binding to CD3+ cells and for enhancing the stability of the resulting mAb, because different FRs can create a different and unexpected pattern of three-dimensional antibody folding that can result in a less stable, less-well-binding, less biologically active mAb. There also should be no a-priori expectation that placing the OKT3 CDRs including the Cys100A mutation in the structural context of humanized de-immunized FRs would result in a humanized mAb with improved biological signaling activity hence improved clinical utility. Moreover, there should be no a-priori expectation that placing the OKT3 CDRs including the Cys100A mutation in the structural context of one particular set of humanized FRs would result in a more biologically active and more stable mAb than placing the CDRs in the context of another set of humanized FRs that differ by only a few amino acids from the other FRs.

The data provided herein for the first time demonstrate that using different FRs with identical CDRs lead to differences in the biological activity and in stability, and that all tested FRs except one have reduced biological activity compared to OKT3 mAb or the Chimeric mAb while maintaining the same binding properties and specificity.

As described in greater detail below, three amino acids were selected to which to mutate Cys100A: alanine (Ala; A), serine (Ser; S) and valine (Val; V), with the aim of retaining, if possible, full binding and biological activity of the anti-CD3 mAb. These mutations resulted in the amino acid sequences described below.

The Orthoclone OKT3™ mAb (Orthoclone, Janssen) is labeled for commercial distribution with a shelf-life of only 9 months, which is a relatively short time period compared to almost all other commercial mAb products. It is hypothesized that this short shelf-life is at partially if not mostly the result of this mAb having an unpaired Cys residue in its CDR3 domain that can promote intermolecular disulfide bond formation or disulfide shuffling and consequent relatively reduced stability of the mAb as described above. Without wishing to be limited by a single hypothesis, it was theorized that mutating the VH CDR3 sequence at Cys100A in order to address this stability issue in the context of humanized de-immunized FRs would result in reduced binding and biological activity of the mutated Cys100A-containing mAb. In an attempt to mitigate this potential problem, three different versions of each variant were produced in order to identify an acceptable level of reduced binding and activity in the context of humanized de-immunized FRs, which themselves would be expected to affect the stability and rigidity of the resulting mAb, and even decrease its stability given that the FRs directly influence the folding hence stability and activity of the mAb including signaling potency.

The humanized de-immunized FRs were selected with the goal of eliminating the immunogenicity of the novel mAb and as a consequence the potential for human anti-human antibody (HAHA) responses, or human anti-mouse antibody (HAMA) responses. The HAMA response is an allergic reaction to immunogenic mouse sequences upon administration of a mouse-derived mAb to a human subject, and the HAHA response is likewise an allergic reaction to immunogenic human sequences upon administration of a humanized or human MAb to a human subject. This response can range from a mild form, e.g., rash, to a more extreme and life-threatening response, such as renal failure. The HAHA/HAMA response also can decrease the effectiveness of the mAb treatment, or create a future immune-based reaction if the patient is given a subsequent treatment containing the same mAb. HAHA/HAMA responses can be readily detected and quantified by conventional immunological techniques, e.g., ELISA.

Specifically, as described in greater detail below, the new mutated mAbs having different FRs, with or without Cys100ASer mutation but otherwise identical, were tested for binding to CD3 on the T-cell surface and for capacity to provide a biological signal for mediating anti-CD3-dependent PBMC proliferation and IL-2 secretion from Jurkat cells. These signaling activities reflect the in-vivo mechanism of oral anti-CD3 immunotherapy, which is to deliver a signal into the T cell that results in immunological changes for inducing Tregs that are favorable for treating autoimmune and inflammatory diseases. The Cys100ASer mutant, which has different FRs from the OKT3 mAb, fully retains the capacity to bind cell-surface CD3. Unexpectedly, the mutant Cys100ASer in the context of OKT3 CDRs, VH1/Vκ1 FRs (VH1ser/Vκ1) and the IgG4/Ser241Pro IgG4 C region was found to have improved biological properties which include, but are not limited to, increased cell signaling activity for both T-cell proliferation of human PBMC and IL-2 secretion from Jurkat cells as compared to the Chimeric mAb (OKT3 VH and VL regions coupled with the IgG4/Ser241Pro C and Cκ region). Furthermore, this VH1ser/Vκ1-containing mAb induces proliferation at a similar level and IL-2 secretion at an even higher level than the original mouse OKT3 mAb, and unexpectedly is more stable than OKT3 or than another humanized mAb VH2ser/Vκ3 that is different from the VH1ser/Vκ1 in only six amino acids in the FRs.

When designing humanized antibodies, without wishing to be limited by a single hypothesis, one of the primary issues is to retain antigen binding equivalent or close to the starting mAb, and an analysis of the sequence and structure of the mAb enables predictions in this regard. Amino acid residues are identified that are believed to be critical for binding, and such residues are maintained in all variants; other residues that are believed to be important are varied between variants. It is often possible to retain equivalent or close to the starting mAb binding. However, there is an additional qualitative component of the binding event, particularly for binding to receptors and providing a stimulus to the target cell that is not solely dependent upon affinity. This qualitative component is impossible to predict and is another reason to make several variants, such that several variants can be tested for their biological effect. There is a search for significant differences in biological effect between Abs that may have only one or two amino acid differences and it is impossible to pin this down to particular variations. The mechanism for this is also unclear, but may be related to the overall stability of the antibody and thus the rigidity of its interaction with its target receptor, which is CD3 in the present invention.

There is a fundamental difference in the properties of rodent and human Abs, in that rodent Abs tend to have tighter associations between the VH and VL domains and the overall structure has greater rigidity. Human Abs tend to be more flexible, which has advantages in that they are more plastic in their binding to antigen. Thus, the improved biological activity observed for the humanized VH1ser/Vκ1 mAb has a unique genesis and properties, one of which is greater IL-2 signaling power, that are non-obvious and unpredictable compared to the mouse OKT3 or to the Chimeric mAb or to other humanized FR variant mAbs described herein or elsewhere.

According to one embodiment, a mAb is disclosed denoted VH1ser/Vκ1 having VH1/Vκ1 frameworks with a Ser residue at position 100A and IgG4 C region with a Ser241Pro mutation. The full-length H- and L-chain amino acid sequences of this mAb are set forth in SEQ ID NOs: 11 and 12 respectively. This mAb is pharmaceutically useful by virtue of having humanized and de-immunized FRs that reduce or eliminate the potential for a HAHA/HAMA response and that increase cell signaling activities for achieving favorable immunological effects, while maintaining cell-surface binding and obviating inappropriate disulfide bond formation, and while enhancing pharmaceutical stability, as described in the Examples.

Definitions

As used herein, the term "treatment" also optionally encompasses reducing the risk of developing, preventing progression, and/or delaying development of such a disease. As used herein, "preventing progression" need not result in 100% prevention of progression in every case, but rather includes delaying or reducing risk of progression. "Therapy" means the administration, by any route, of a mAb to CD3, or a fragment thereof comprising at least the V regions, as described herein. "Oral or mucosal therapy" means the administration of molecule mAb or a fragment thereof as described herein orally or to a mucosal membrane (or a combination thereof).

Monoclonal antibodies (mAbs) according to the invention include whole Abs, or active (antigen-binding) fragments thereof comprising at least the V regions (e.g., F(ab')$_2$, scFv, etc.).

"Signaling activity of anti-CD3 mAb" means herein that following cell binding, the anti-CD3 mAb exerts its biological activity for stimulating immunological effector functions through signals to T cells for stimulating transformation to Tregs. The capacity of novel anti-CD3 mAbs to support T-cell proliferation and cellular signaling can be evaluated using human peripheral blood mononuclear cells (PBMC), or by measuring the cellular signaling activity of different antibody variants to stimulate IL-2 secretion by cultured cell lines such as Jurkat cells. This enhanced signaling activity, which can be measured by quantifying cytokine secretion in vitro, also occurs in vivo and is expected to affect T-cell proliferation and result in the production of Tregs, which are measured in mouse models and in human clinical trials and which correlate with improved disease status after oral administration of anti-CD3 mAb.

"Disease that is susceptible to amelioration by binding to CD3" means any disease selected from the group including an autoimmune or inflammatory disease. According to one specific embodiment the disease is hepatitis. Treatment of such disease may optionally include therapeutic or prophylactic administration, optionally before the onset of one or more symptoms. The compositions described herein, comprising mAbs to CD3, can be administered to a subject, e.g. by oral or mucosal routes, to treat such disorders by inducing Tregs.

Examples of autoimmune and inflammatory diseases and disorders which are treatable with the mAbs of the present invention include, but are not limited to, Alopecia Areata, Lupus (SLE), Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type 1 diabetes, T1D), non-Insulin-Dependent Diabetes (Type 2 diabetes, T2D), Vasculitis, Lichen Planus, Vitiligo, and Hepatitis. The oral anti-CD3 antibody compositions described herein can be administered to a subject to treat and optionally to prevent disorders associated with an abnormal or unwanted immune response associated with cell, tissue or organ transplantation, e.g., renal, hepatic, and cardiac transplantation, e.g., graft-versus-host disease (GVHD), or to reduce the risk of allograft rejection.

The term "Hepatitis" refers to any inflammation of the liver. Non-limiting examples of causes of Hepatitis include infectious agents (including but not limited to viruses such as hepatitis A, B, C, D and E; herpes viruses such as herpes simplex virus [HSV] or cytomegalovirus [CMV] or Epstein-Barr virus [EBV]; and other viruses such as yellow fever virus, human immunodeficiency virus [HIV], and adenoviruses; non-viral infectious agents such as toxoplasma, Leptospira, Q fever and Rocky Mountain spotted fever; or any infectious agent resulting in hepatitis); toxins (including any toxic substance or any substance which is toxic to the liver with excessive intake, such as alcohol or medicines, for example due to any drug-associated liver injury (DALI), including acetaminophen or any other drug that leads to liver damage); non-alcoholic steatohepatitis (NASH), which is typically caused or exacerbated by obesity or diabetes, or a combination of these two conditions; liver disease associated with inflammatory bowel disease; hyperlipidemia, whether as the primary or only cause, or in association with NASH; and as a consequence of vascular disorders; or hepatitis of other etiology.

The term "subject" refers to human patients for whom it is desired to treat using the methods according to the present invention. However, it will be understood that "patient" does not automatically imply that symptoms or diseases are present. As used herein, the term "patient" preferably refers to a human in need of treatment.

The term "treatment" as used herein refers to therapeutic treatment of a disease or disorder in a subject. In some embodiments, the term treatment also refers to prophylactic or preventive measures as discussed above. Those in need of treatment include those already with the disorder as well as those in which the disorder is to be prevented (i.e., in which risk of developing the disorder is to be reduced). Hence, a subject to be treated herein may have been diagnosed as having the disorder or may be (i.e., have been identified as) predisposed or susceptible to the disorder. Thus the term "treatment" or "treating" herein encompasses curative treatment (although a 100% cure in all subjects is not required), prophylactic treatment as well as palliative treatment, more specifically palliative treatment and curative treatment.

The phrase "pharmaceutically acceptable" refers to molecular entities and compositions that are physiologically tolerable and do not typically produce an allergic or similar untoward reaction, such as gastric upset, dizziness and the like, when administered to a patient in particular to a human.

The expression "effective amount" is an amount sufficient to effect beneficial or desired clinical results including, without limitation, preventing (reducing risk of) progression or development of, or attenuating symptoms resulting from, the disease, and decreasing the dose of other medicaments required to treat the disease. An effective amount can be administered in one or more administrations of the active substance.

The term "antigen" refers to a molecule or a portion of a molecule capable of being bound by a selective binding agent, such as an antibody. An antigen may have one or more epitopes.

The term "antibody" (Ab), as used herein, refers to a protein which may be produced by the immune system that binds to an antigen. But as used herein, the term encompasses not only intact mAbs but also antigen-binding fragments thereof comprising at least the V regions as defined in the present invention, single chains, mutants thereof, naturally occurring variants, fusion proteins, and any other modified configuration of the immunoglobulin molecule that comprises the V regions, as well as mAbs produced by mammalian or bacterial cells that carry antibody-coding DNA sequences, and also recombinant mAbs that are made in host cells or transgenic animals carrying the genes coding for the recombinant mAbs.

The terms "antibody" (Ab) or "antibodies" (Abs) and "immunoglobulins" (Igs) refer to glycoproteins having the same structural characteristics. While Abs exhibit binding specificity to a specific antigen, Igs include both Abs and other antibody-like molecules that lack known antigen specificity. Polypeptides of the latter kind are, e.g., produced at low levels by the lymphoid system and at increased levels by myelomas.

Antibodies or immunoglobulins as used herein also comprise heterotetrameric glycoproteins of about 150 kilodaltons, composed of two identical L chains and two identical H chains. Each L chain is linked to a H chain by one disulfide bond, while the number of disulfide linkages varies between H chains of different Ig isotypes. Each H and L chain also has regularly spaced intrachain disulfide linkages. Each H chain has at its amino-end a VH followed by a number of CH domains. Each L chain has a VL domain at its amino-end and one CL domain at its other end; the CL domain is aligned with the first CH domain, and the VL domain is aligned with the VH domain. Particular amino acid residues form an interface between the VH and VL domains (Chothia et al, J. Mol. Biol. 186: 651, 1985; Novotny and Haber, Proc Natl Acad Sci USA, 82: 4592, 1985; Chothia et al, Nature 342: 877, 1989).

The VH and VL regions can be further subdivided into regions of hypervariability, termed CDRs, interspersed with regions that are more conserved, termed FRs. Each VH and VL is composed of three CDRs and four FRs, arranged from amino-terminus to carboxyl-terminus in the following order: FR1, CDR1, FR2, CDR2, FR3, CDR3, FR4.

The VH and VL domains together contain a binding domain (composed of CDRs) that interacts with and binds to an antigen. The sites of greatest interest for modifications to affect the binding properties of the Ig include the hypervariable loops (CDRs), but FR alterations are also contemplated. CDR residues or FR residues involved in antigen binding and antibody biological effects are generally substituted in a relatively conservative manner. Some FR residues are thought to have a significant effect on antigen binding and biological activity in at least three ways: by noncovalently binding directly to an epitope, by interacting with one or more CDR residues, and by affecting the interface between the H and L chains. The effects of FR sequence changes cannot be predicted. Some of these amino acid residue changes in different FRs in the same Ab chain or in different chains may be positioned close together in actual three-dimensional space and may have unpredictable unique cumulative influences that can be tested empirically only by biochemical, in vitro, and in vivo assays. The CH and CL domains are not directly involved in antigen binding but mediate various Ig effector functions, such as participation of the Ab in antibody-dependent cellular cytotoxicity (ADCC), complement-dependent cytotoxicity (CDC) and antibody-dependent cellular phagocytosis (ADCP). In this regard, the C regions may mediate the binding of the Ig molecule to host tissues or factors, including various cells of the immune system (e.g., effector cells).

The term "Kabat numbering scheme" is a widely-adopted standard for numbering the amino residues of an Ab in a consistent manner, see, e.g., bioinf.org.uk/abs (Wu T T and Kabat, E A. J Exp Med 132, 211-50, 1970; and Kabat E A et al. Sequences of Proteins of Immunological Interest, Fifth Edition. NIH Publication No. 91-3242, 1991). It is based on sequence variability and is most commonly used to define the CDR sequence.

The terms "monoclonal antibody" (mAb) or "monoclonal antibody composition" as used herein refer to a preparation of antibody molecules of a single molecular composition. A mAb composition displays a single binding specificity and affinity for a specific epitope.

The term "epitope" means a protein determinant capable of specific binding to an Ab. Epitopes usually consist of chemically active surface groupings of molecules such as amino acids or sugar side chains and usually have specific three-dimensional structural characteristics, as well as specific charge characteristics.

The phrases "an antibody recognizing an antigen" and "an antibody specific for an antigen" are used interchangeably herein with the term "an antibody which binds specifically to an antigen."

The term "antigen-binding portion" of an Ab (or simply "antibody portion" or "antibody fragment"), as used herein, refers to one or more fragments of an intact Ab that retain the ability to bind specifically to CD3 or an interaction thereof as described above. It has been shown that the antigen-binding function of an Ab can be performed by fragments of a full-length Ab. Examples of binding include, but are not limited to: (i) a Fab fragment, a monovalent fragment consisting of the VL, VH, CL and CH1 domains; (ii) a F(ab)'$_2$ fragment, a bivalent fragment comprising two Fab fragments linked by a disulfide bridge at the hinge region; (iii) a Fv fragment consisting of the VL and VH domains of a single arm of an antibody, (iv) a dAb fragment (Ward et al, Nature 341: 544-6, 1989), which consists of a VH domain; Furthermore, although the VL and VH domains of the Fv fragment are encoded by separate genes, they can be joined using recombinant methods by a synthetic linker that enables them to be made as a single protein chain in which the VL and VH regions pair to form monovalent molecules (known as single chain Fv (scFv); see e.g., Huston et al, Proc Natl Acad Sci USA 85: 5879-83, 1988). Such single chain Abs are also intended to be encompassed within the term "antigen-binding portion" of an Ab. These Ab fragments are obtained using conventional techniques known to those with skill in the art, and the fragments are screened for utility in the same manner as are intact Abs.

The term "fragments" as used herein refers to sequences sharing at least 10% amino acids in length with the respective sequence of the intact or full length Ab. These sequences can be used as long as they exhibit the same antigen binding properties as the Ab sequence from which they derive. In some embodiments, a fragment can be at least 6 amino acids in length, and can be, for example, at least 8, at least 10, at least 14, at least 16, at least 20 or at least 25 amino acids or greater than 25 amino acids from the full-length protein from which the fragment was derived. In some embodiments, the term fragment encompasses at least 6, 10, 20, 50, 100, 250, 500 amino acids from the full length protein from which the fragment was derived. Exemplary fragments include C-terminal truncations, N-terminal truncations, or truncations of both C- and N-terminals (e.g., deletions of 1, 2, 3, 4, 5, 10, 15, 20, 30, 40, 50, 75, 100 or more amino acids deleted from the N-termini, the C-termini, or both). Preferably these sequences share >90% homology in amino acid sequence with the respective sequence of the intact or full length antibody, e.g., mAbs. In some embodiments, the term "fragments" as used herein, when used in reference to mAb fragments or antigen-binding portions or fragments, usually refers to a portion of at least 2, or at least about 5, or at least about 7, or at least about 10 or more consecutive amino acids of the epitope binding region of an Ab. In some embodiments, a fragment includes at least 2, or at least about 5, or at least about 7, or at least about 10 or more consecutive amino acids of the epitope binding region of an Ab having a sequence as described herein. In some embodiments, the fragment is a functional fragment, where a "functional fragment" as used in the context of a "functional fragment of an antibody" refers to a fragment of the Ab that mediates the same effect as the full-length Ab, e.g., specifically binds to the same antigen with the same or higher affinity compared to the full-length Ab.

Suitable Abs, e.g., mAb or fragments of the invention, are active, i.e., are immunologically functional Igs. The term "immunologically functional immunoglobulin fragment" as used herein refers to a Ig fragment that binds to CD3.

The term "de-immunized" as used herein refers to an Ab whose V regions have been chosen to lack T-cell epitopes or altered to remove T-cell epitopes, thereby minimizing or eliminating the potential for the Ab to be immunogenic.

The term 'HAMA' (human anti-mouse antibody) refers to Abs formed by a human subject that will bind to mouse-derived Ig sequences in an Ab that is administered to said subject.

The term 'HAHA' (human anti-human antibody) refers to Abs formed by a human subject that will bind to human-derived Ig sequences in an Ab that is administered to said subject.

In some embodiments, the present invention concerns a method for producing one or more mAbs or isolated mAb fragments. In some embodiments, such an Ab can also be produced by a method comprising the steps of:

(a) producing a preparation of an antigen related to human CD3, or a fragment, or a cell containing CD3 or a fragment, or a fusion protein thereof;

(b) immunizing a rodent, e.g., a mouse, with the antigen, or a fragment, or a fusion protein thereof, or a cell containing said antigen;

(c) detecting specifically binding or blocking Abs in the serum of the mice;

(d) producing hybridomas between lymph node cells from the mice and myeloma cells to produce Abs; and (e) screening hybridomas with an antigen-specific binding assay.

In some embodiments, an antigen used to produce Abs is human or from a subhuman primate species.

In some embodiments, the antigen used to produce Abs is a primary cell or cell line expressing endogenous or recombinant full length antigen or an antigenic fragment of the antigen, or a fusion protein of all or part of the antigen and another protein, or the antigen is part of a virus-like particle.

In some embodiments, the antigen used to produce Abs is expressed in a cell line syngeneic with mice of step (b), or the antigen used to produce Abs is fused to the Fc portion of an IgG.

In some embodiments, the antigen used to produce Abs is human or mouse antigen fused to the Fc portion of human IgG1.

In some embodiments, the antigen used to produce Abs is on the surface of cells.

As an alternative to steps b), c) and d), an Ab, or fragment thereof comprising at least the V regions, can be obtained by selecting Ab sequences by phage display on the antigen of step a).

In some embodiments, the binding assay of step (e) is carried out by applying visualizing methods comprising enzyme-linked immunosorbent assay (ELISA), dot blot, immunoblot, immunoprecipitation, flow cytometry, fluorescence microscopy, confocal microscopy, calorimetry, surface plasmon resonance, Ouchterlony test, complement-mediated lysis of red blood cells, ADCC and the like. Preferably the binding assay for a mAb is carried out by direct or capture ELISA or flow cytometry.

In particular, Abs can be purified by, e.g., protein A or G or L affinity chromatography, anti-mouse IgG Ab-based affinity chromatography, ion exchange, ethanol or ammonium sulfate precipitation, and the like.

Methods for preparing an immunogen and immunizing an animal are well-known in the art (Kohler and Milstein, Nature 256: 495-7, 1975; Brown et al, J Immunol 127: 539-46, 1981; Brown et al, J Biol Chem 255: 4980-3, 1980; Yeh et al, Proc Natl Acad Sci USA 76: 2927-31, 1976; Yeh et al, Int J Cancer 29: 269-75, 1982; Kozbor et al, Immunol Today 4:72, 1983; Cole et al, Monoclonal Antibodies and Cancer Therapy, Alan R. Liss, Inc., pp. 77-96, 1985; U.S. Pat. No. 4,816,567; Clackson et al, Nature 352: 624-8 1991; Marks, et al J Mol Biol 222: 581-97, 1991).

According to some embodiments of the present invention, there are provided host cells comprising an expression vector containing a DNA segment encoding a signal peptide, consensus H or L region signal sequences, and a DNA segment encoding and expressing an anti-CD3 mAb as described herein, e.g., a mAb or isolated mAb fragments thereof, as well as transgenic animals having a genome comprising said isolated DNA segment and/or the expression vector.

The terms "expression vector" and "recombinant expression vector" as used herein refer to a DNA molecule, for example a plasmid or modified virus, containing a desired and appropriate nucleic acid sequence necessary for the expression of the recombinant polypeptides in a host cell. As used herein, "operably linked" refers to a functional linkage of at least two sequences. Operably linked includes linkage between a promoter and a second sequence, for example a nucleic acid of the present invention, wherein the promoter sequence initiates and mediates transcription of the DNA sequence corresponding to the second sequence.

The regulatory regions necessary for transcription of the polypeptides can be provided by the expression vector. The precise nature of the regulatory regions needed for gene expression may vary among vectors and host cells. Generally, a promoter is required which is capable of binding RNA polymerase and promoting the transcription of an operably-associated nucleic acid sequence. Regulatory regions may include those 5' non-coding sequences involved with initiation of transcription and translation, such as the TATA box, cap sequence, CAAT sequence, and the like. The non-coding region 3' to the coding sequence may contain transcriptional termination regulatory sequences, such as terminators and polyadenylation sites. A translation initiation codon (ATG) may also be provided. The vector design for mammalian expression cells may contain leader sequences, one common for the H chain and one common to the L chain, for enabling high levels of mAb expression and secretion. The N-terminal peptide signal sequence is initially synthesized on the ribosome which is recognized by the signal recognition particle (SRP) that stalls mRNA translation while the ribosome is docked via the signal sequence to the SEC61 translocon at which point the SRP is dissociated and mRNA translation resumes with the feeding of the polypeptide into the ER. The signal sequence thus can play a crucial role in the synthesis of mAbs.

In order to clone the nucleic acid sequences into the cloning site of a vector, linkers or adapters providing the appropriate compatible restriction sites are added during synthesis of the nucleic acids. For example, a desired restriction enzyme site can be introduced into a fragment of DNA by amplification of the DNA by use of PCR with primers containing the desired restriction enzyme site.

An alternative method to PCR is the use of a synthetic gene. The method allows production of an artificial gene that comprises an optimized sequence of nucleotides to be expressed in host cells of a desired species (e.g., CHO cells or E. Coli). Redesigning a gene offers a means to improve gene expression in many cases. Rewriting the open reading frame (ORF) is readily possible because of the redundancy of the genetic code. Thus, it is possible to change up to ~30% of the nucleotides in an ORF and still produce the same protein. For a typical protein sequence of 300 amino acids, there are >10150 codon combinations that will encode an identical protein. Using optimization methods such as replacing rarely used codons with more common codons can result in dramatic improvements in expression level. Further optimizations such as removing RNA secondary structures also can be included. Computer programs are available to perform these and other simultaneous optimizations. A well-optimized gene can dramatically improve protein expression. Because of the large number of nucleotide changes made to the original DNA sequence, the only practical way to create the newly designed gene is to use gene synthesis.

An expression construct comprising a polypeptide sequence operably associated with regulatory regions can be directly introduced into appropriate host cells for expression and production of polypeptide per se or as a recombinant fusion protein. The expression vectors that may be used include but are not limited to plasmids, cosmids, phage, phagemids or modified viruses. Such expression vectors typically comprise a functional origin of replication for propagation of the vector in an appropriate host cell, one or more restriction endonuclease sites for insertion of the desired gene sequence, and one or more selection markers.

The recombinant polynucleotide construct comprising the expression vector and a polypeptide according to the invention is transferred into an appropriate prokaryotic or eukaryotic host cell where it can replicate (e.g., a bacterial cell), and be transcribed. This can be accomplished by methods known in the art. The expression vector is used with a compatible prokaryotic or eukaryotic host cell which may be derived from bacteria, yeast, insects, mammals and humans.

The term "mutant" or "variant" as used herein in reference to an amino acid, DNA or RNA sequence means that such a sequence differs from, but has sequence identity with, the wild-type or disclosed sequence. The degree of sequence identity between the wild-type or disclosed sequence and the mutant sequence is preferably greater than about 70%, 80%, 90%, 95%, 98%, or more.

The amino acid residues referred to herein encompass the natural coded amino acids represented by either one-letter or three-letter codes according to conventions well known in the art. In chemical synthesis, amino acid derivatives and D isomers can also be used. In chemical synthesis, sequential, divergent and convergent synthetic approaches to the peptide sequence may be used.

The terms "protein" and "polypeptide" are used interchangeably herein to refer to amino acids joined to each other by peptide bonds or modified peptide bonds, i.e., peptide isosteres, and may contain modified amino acids other than the 20 gene-encoded amino acids. The polypeptides may be modified by natural processes, such as post-translational processing, or by chemical modification techniques that are well known in the art. Pre- or post-translational modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications.

Modifications of polypeptides and amino acids include acetylation; acylation; ADP-ribosylation; amidation; covalent attachment of non-peptide molecules such as flavin, a heme moiety, a nucleotide or nucleotide derivative, a lipid or lipid derivative, or a phosphytidylinositol; cross-linking cyclization; disulfide bond formation; demethylation; formation of covalent cross-links; formation of cysteine; formation of pyroglutamate; formylation; gamma-carboxylation; glycosylation; GPI anchor formation; hydroxylation; iodination; methylation; myristolyation; oxidation; pegylation; proteolytic processing; phosphorylation; prenylation; racemization; selenoylation; sulfation; and transfer-RNA mediated addition of amino acids to protein such as arginylation (see, e.g., Creighton T E, Proteins-Structure and Molecular Properties 2nd Ed., W. H. Freeman and Company, New York, 1993; Posttranslational Covalent Modification of Proteins, B. C. Johnson, Ed., Academic Press, New York, pp. 1-12, 1983).

As used herein, "heterologous" refers to two biological components that are not found together in nature. The components may be proteins or fragments thereof, host cells, genes or control sequences such as promoters. Although the heterologous components are not found together in nature, they can function together, such as when a promoter heterologous to a gene is operably linked to the gene.

The terms "polynucleotide", "nucleic acid sequence" and "nucleic acid" are used interchangeably herein to refer to polymeric forms of nucleotides of any length, either ribonucleotides or deoxynucleotides, including but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Further included are mRNA or cDNA that comprise intron sequences (see, e.g., Niwa et al, Cell 99: 691-702, 1999). The backbone of the polynucleotide can comprise sugars and phosphate groups (as typically be found in RNA or DNA), or modified or substituted sugar or phosphate groups. Alternatively, the backbone of the polynucleotide can comprise a polymer of synthetic subunits such as phosphoramidites and thus can be an oligodeoxynucleotide phosphoramidate or a mixed phosphoramidate-phosphodiester oligomer (see, e.g., Peyrottes et al, Nucl Acids Res 24: 1841-8, 1996; Chaturvedi et al, Nucl Acids Res 24: 2318-23, 1996). Polynucleotides may comprise modified nucleotides, such as methylated nucleotides and nucleotide analogs, uracil, other sugars, and linking groups such as fluororibose and thioate, and nucleotide branches. The sequence of nucleotides may be interrupted by non-nucleotide components. A polynucleotide may be further modified after polymerization, such as by conjugation with a labeling component, capping, substitution of one or more of naturally occurring nucleotides with an analog, and introduction of means for attaching the polynucleotide to proteins, metal ions, labeling components, other polynucleotides, or a solid support.

The terms "coding sequence of" and "coding region of", in reference to a particular polypeptide or protein, are used interchangeably herein to refer to a nucleic acid sequence which is transcribed and translated into the particular polypeptide or protein when placed under the control of appropriate regulatory sequences.

The term "polynucleotide sequence encoding a polypeptide" encompasses a polynucleotide which includes only coding sequence for the polypeptide, as well as a polynucleotide which includes additional coding and/or non-coding sequence. Examples of additional coding sequences include leader or secretory sequences. Examples of non-coding sequences or regulatory sequences, such as promoters, transcription enhancers, etc., are well known in the art.

The term "identity", as used herein and as known in the art, is a relationship between two or more polypeptide sequences or two or more polynucleotide sequences, as determined by comparing the sequences. The term "identity" also means the degree of sequence relatedness between polypeptide or polynucleotide sequences, as the case may be, as determined by the match between strings of such sequences. "Identity" and "similarity" can be readily calculated by known methods (described, e.g., in, Computational Molecular Biology, Lesk A M, ed., Oxford University Press, New York, 1988; Biocomputing: Informatics and Genome Projects, Smith D W, ed., Academic Press, New York, 1993; Computer Analysis of Sequence Data, Part I, Griffin A M and Griffin H G eds., Humana Press, N.J., 1994; Sequence Analysis in Molecular Biology, von Heinje G, Academic Press, 1987; Sequence Analysis Primer, Gribskov M and Devereux J eds., M Stockton Press, New York, 1991; Carillo H and Lipman D, SIAM J. Applied Math 1988, 48: 1073).

Preferred methods to determine identity are designed to give the largest match between the tested sequences. Methods to determine identity and similarity are codified in publicly available computer programs. Preferred program methods to determine identity and similarity between two sequences include, but are not limited to, the GCG program package (Devereux et al, Nucl Acids Res 24: 2318-23, 1984), BLASTP, BLASTN, and FASTA (Atschul et al, J Molec Biol 215: 403-10, 1990). The BLAST X program is publicly available from NCBI and other sources (BLAST Manual, Altschul et al, NCBI NLM NIH Bethesda, Md. 20894; Altschul et al, J Molec Biol 215: 403-10, 1990). As an illustration, by a polynucleotide having a nucleotide sequence having at least, e.g., 95% "identity" to a reference nucleotide sequence, it is intended that the nucleotide sequence of the tested polynucleotide is identical to the reference sequence over its full length. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into or deleted from the reference sequence. These mutations of the reference sequence may occur at the 5'- or 3'-terminal positions of the reference DNA sequence or anywhere between those terminal positions, interspersed either individually among nucleotides in the reference sequence or in one or more contiguous groups within the reference sequence. Analogously, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into or deleted from the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

The phrase "substantially identical" in the context of two nucleic acids or polypeptides, refers to two or more sequences that have at least 70%, 80%, and in some aspects 90-95% nucleotide or amino acid residue identity, when compared and aligned for maximum correspondence, as measured using one of the known sequence comparison algorithms or by visual inspection. In some embodiments, the sequences are substantially identical over the entire length of the coding regions.

A "substantially identical" amino acid sequence is one that differs from a reference sequence by one or more conservative or non-conservative substitutions, deletions or insertions, provided that the polypeptide generally retains its functional and/or immunogenic and/or antibody-binding properties. A conservative amino acid substitution, for example, substitutes one amino acid residue for another of the same chemical class (e.g., substitution of a hydrophobic residue for another, e.g., isoleucine, valine, leucine, or methionine; or substitution of a polar residue for another, e.g., arginine for lysine, glutamic acid for aspartic acid, or glutamine for asparagine).

The term "oligonucleotide" or "polynucleotide" refers to a single-stranded polydeoxynucleotide or two complementary polydeoxynucleotide strands that may be chemically synthesized. Synthetic oligonucleotides generally lack 5'-phosphate and thus will not ligate to another oligonucleotide without adding a phosphate with an ATP in the presence of a kinase.

The term "primer" as used herein refers to an oligonucleotide which is capable of acting as a point of initiation of nucleic acid synthesis when placed under conditions in which synthesis of a primer extension product which is complementary to a nucleic acid strand is induced, i.e., in the presence of nucleotides and an inducing agent such as DNA polymerase and at a suitable temperature and pH. Primer sequences may be obtained from a biological source such as a purified restriction digest of genomic DNA, or may be produced synthetically. The primers are preferably single-stranded for maximum efficiency in amplification, but alternatively may be double-stranded. If double-stranded, the primer is first treated to separate its strands before being used to prepare amplification products. Preferably, the primers are oligodeoxyribonucleotides but must be sufficiently long to prime the synthesis of extension products in the presence of the inducing agent. The exact lengths of the primers will depend on many factors, including temperature, source of primer and use of the method. The primers typically contain 10 or more nucleotides.

Synthetic oligonucleotide primers may be prepared using any suitable method, such as, e.g., the phosphotriester and phosphodiester methods (Narang et al, Meth. Enzymol. 68: 90, 1979; Brown et al, Meth. Enzymol. 68: 109, 1979) or automated embodiments thereof. In one such automated embodiment, diethylphosphoramidites are used as starting materials and may be synthesized (Beaucauge et al, Tetrahedron Let. 22: 1859-62, 1981). One method for synthesizing oligonucleotides on a modified solid support is described in U.S. Pat. No. 4,458,066 which is incorporated herein by reference.

The term "digestion" in reference to a nucleic acid, in particular a DNA molecule, refers to catalytic cleavage of the DNA with a restriction enzyme that acts only at certain sequences in the DNA. The various restriction enzymes used herein are commercially available and their reaction conditions, cofactors and other requirements may be readily ascertained by the ordinarily skilled artisan. After digestion, gel electrophoresis may be performed to isolate the desired fragment, the latter of which is also referred to as a "restriction fragment".

As used herein, the term "isolated" means that the material is removed from its original environment. The original environment may be a natural environment if the material is naturally occurring, for example in a bacterial cell wall, or the original environment may be an artificial environment, if the material is artificial or engineered. For example, a naturally occurring polynucleotide or polypeptide present in a living organism, when separated from some or all of the coexisting materials in the natural system, is isolated. Similarly, a recombinantly engineered polynucleotide or the corresponding expressed polypeptide, are referred to as isolated, when separated from a vector or expression system respectively containing the recombinant polynucleotide or expressed polypeptide.

As used herein, the term "purified" does not require absolute purity; rather, it is intended as a relative definition. The purified nucleic acid sequences of the invention have been purified from other sequences, such as the remainder of genomic DNA or from other sequences in a library or other environment by at least one order of magnitude, typically two or three orders, and more typically four or five orders of magnitude, to a sufficient degree that enables further manipulation of the specific DNA sequence.

As used herein, the term "recombinant", in reference to a nucleic acid, means that the nucleic acid is adjacent to a "backbone" nucleic acid to which it is not adjacent in its natural cellular or viral environment. Backbone molecules according to the invention include nucleic acids such as expression vectors, self-replicating nucleic acids, viruses, integrating nucleic acids, and other vectors or nucleic acids used to maintain or manipulate a nucleic acid insert of interest.

As used herein, the term "recombinant", in reference to polypeptides or proteins, means polypeptides or proteins produced by recombinant DNA techniques, i.e., produced from prokaryotic or eukaryotic cells transformed by a DNA construct encoding the desired polypeptide or protein.

As used herein, "host cell" refers to a cell that has been transfected or is capable of transfection by an exogenous polynucleotide sequence, either in the form of a recombinant vector or other transfer DNA, and includes the progeny of the original cell which has been transfected or transformed.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include, at a minimum, all components whose presence is necessary for expression, and may also include additional components whose presence is advantageous, e.g., leader sequences.

As used herein, the term "operably linked" refers to sequences joined or ligated to function in their intended manner. For example, a control sequence is operably linked to a coding sequence by ligation in such a way that expression of the coding sequence is achieved under conditions compatible with the control sequence and the host cell. For example, a promoter sequence is "operably linked to" a coding sequence when RNA polymerase, which initiates transcription at the promoter, will transcribe the coding sequence into mRNA.

As used herein, the term "synthetic", in reference to polypeptides or protein sequences, means those that are those prepared by chemical synthesis. Sequential, divergent and convergent synthetic approaches may be used in chemical synthesis.

Novel Antibodies

The term "antibody" (Ab) as used herein refers to an Ig molecule or immunologically active portion thereof that is readily derived by means of known techniques of protein chemistry and recombinant DNA engineering, i.e., an antigen-binding portion. Non-limiting examples of immunologically active portions of Ig molecules include F(ab) and F(ab')$_2$ fragments, which include the specific mutations to the FR, the Cys100ASer point mutation in CDR3 of the VH domain, and the VH1/Vκ1 FRs, and that retain the ability to bind CD3. Such fragments can be obtained commercially or by using methods known in the art. For example F(ab)$_2$ fragments can be generated by treating the antibody with an enzyme such as pepsin, a non-specific endopeptidase that normally produces one F(ab)$_2$ fragment and numerous small peptides of the Fc portion. The resulting F(ab)$_2$ fragment is composed of two disulfide-connected Fab units. The Fc fragment is extensively degraded and can be separated from the F(ab)$_2$ using methods known in the art, e.g., by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50-kilodalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). Commercially available services for generating antigen-binding fragments also can be used, e.g., services provided by BioExpress, West Lebanon, N.H.

In some embodiments, the Ab has reduced or no ability to bind an Fc receptor. For example, the Ab can be an isotype or subtype, fragment or other mutant, which does not support binding to an Fc receptor, e.g., it has a mutagenized or deleted Fc receptor binding region. The Ab can be coupled to a toxin or imaging agent.

Methods for making such Abs are also known; a non-limiting exemplary description is provided below with regard to Example 1.

Ab humanization techniques are known in the art. Typically, successful "humanization" results in a less immunogenic or non-immunogenic mAb with acceptable retention of the antigen-binding properties of the original mAb. In order to retain the antigen-binding properties of the original mAb, the structure of its antigen-combining site needs to be faithfully reproduced in the humanized version. This can potentially be achieved by transplanting the CDRs of the nonhuman Ab onto a human V region FR, either (a) by grafting the entire nonhuman VH and VL domains onto human C regions to generate a chimeric mAb (Morrison et al, Proc Natl Acad Sci USA 81: 6801, 1984; Morrison and Oi, Adv Immunol 44: 65, 1988) which preserves the ligand-binding properties, but which also retains the immunogenicity of the nonhuman V domains; (b) by grafting only the nonhuman CDRs onto human FR and C regions with or without retention of critical FR residues (Jones et al, Nature, 321: 522, 1986; Verhoeyen et al, Science 239: 1539, 1988); or (c) by transplanting the entire nonhuman V domains (to preserve ligand-binding properties) but also "cloaking" them with a human-like surface through judicious replacement of exposed residues to reduce antigenicity) (Padlan, Molec Immunol 28: 489, 1991).

The Ab also can be an engineered scFV (Colcher et al, Ann NY Acad Sci 880: 263-80, 1999; Reiter, Clin Cancer Res 2: 245-52, 1996). The single-chain Ab can be dimerized or multimerized to generate multivalent Abs having specificities for different epitopes of the same target protein. In some embodiments, the Ab is monovalent (e.g., Abbs et al, Ther Immunol 1: 325-31, 1994).

The mAb also can be bispecific, meaning that one arm of the Ig molecule is specific for binding to CD3 and the other arm of the Ig molecule has a different specificity that can enhance the biological activity of the mAb. In this regard, a multi-specific antibody is also considered to be at least bispecific. The mAb also can be multi-specific in the sense of being multivalent.

The term "selectively binds" in reference to an Ab does not mean that the antibody only binds to a single substance. Rather, it denotes that the Kd of the Ab to a first epitope is greater than the Kd of the Ab to a second epitope. Abs that exclusively bind to an epitope only bind to that single epitope.

According to another embodiment of the present invention, there are provided isolated mAbs or fragments or antigen-binding portions or fragments thereof obtainable by the above-described process and wherein said isolated mAbs or isolated mAb fragments or antigen-binding portions or fragments thereof bind to human CD3 expressed on the surface of Jurkat cells with known binding curve and can compete with labeled OKT3 mAb. In some embodiments, an Ab or fragment or antigen-binding portion thereof as disclosed herein specifically binds to CD3 with affinity similar to that of OKT3.

The mAb is de-immunized by selecting or engineering FR domains to be without T-cell epitopes, which if present in the mAb sequence would enable the human subject to make a HAHA/HAMA response against the mAb, resulting in an immune-mediated reaction that causes AEs in human subjects or diminished treatment effectiveness.

Dosage, toxicity and therapeutic efficacy of such Ab compositions can be determined by standard pharmaceutical procedures in cell cultures (e.g., of cells taken from an animal after administration of Ab) or experimental animals, e.g., for determining $LD_{50}$ (the dose lethal to 50% of the study group) and $ED_{50}$ (the dose therapeutically effective in 50% of the study group). The ratio between toxic and therapeutic effects is the therapeutic index and can be expressed as the ratio $LD_{50}/ED_{50}$. Compositions with high therapeutic indices are preferred.

The data obtained from the cell cultures (e.g., cells taken from an animal after Ab administration) and animal studies can be used to formulate a range of dosage levels for humans. The dosage of Ab compositions lies preferably within a range of therapeutically available concentrations that include the $ED_{50}$ with little or no toxicity. The dosage may vary within this range depending upon the dosage form employed and the route of administration utilized. For any Ab compositions used in the methods described herein, the therapeutically effective dose can be estimated initially from assays of cell cultures. A dose also may be formulated in animal studies based on efficacy in suitable animal models. Such information can be used to more accurately determine useful human doses.

As defined herein, a therapeutically effective amount of Ab (i.e., effective dosage) depends on the Ab selected, mode of delivery, and condition to be treated. For instance, in some embodiments single-dose amounts of Ab in the range of ~1 to 100 mg/kg may be administered. In some embodiments, e.g., in pediatric subjects, a lower amount of Ab can be administered. The Ab compositions can be administered from one or more times per week or per month or per year, including, e.g., daily or weekly. The skilled artisan will appreciate that certain factors may influence the dosage and timing required to effectively treat a subject, including but not limited to the nature of the Ab formulation, severity of the disease or disorder, type of disease or disorder, previous treatments, the general health and/or age of the subject, other diseases present, and persistence of the therapeutic effect.

Treatment of a subject with a therapeutically effective amount of the mAb may optionally include a single treatment or a series of treatments. The pharmaceutical composition can be included in a container, pack, or dispenser with dosing instructions.

Pharmaceutical Compositions

According to at least some embodiments of the present invention, there are provided pharmaceutical compositions comprising the Abs described herein. Such compositions will typically be formulated for compatibility with their intended route of administration. For example, pharmaceutical compositions suitable for injection are typically buffered liquid formulations.

Pharmaceutical compositions suitable for oral administration are typically solid dosage forms (e.g., capsules or tablets) or liquid preparations (e.g., solutions, suspensions, emulsions, or elixirs). Solid oral dosage forms are desirable for ease of determining and administering defined dosage of active ingredient, and ease of administration, particularly administration by the subject at home.

Liquid oral dosage forms also allow subjects to easily take the required dose of active ingredient; liquid preparations can be prepared as a drink, or to be administered, for example, by a naso-gastric tube. Liquid oral pharmaceutical compositions generally require a suitable solvent or carrier system in which to dissolve or disperse the active agent, thus enabling the composition to be administered to a subject. A suitable solvent system is compatible with the active agent and non-toxic to the subject. Typically, liquid oral formulations use a water-based solvent.

The oral compositions can also optionally be formulated to reduce or avoid the degradation, decomposition, or deactivation of the active agent by the gastrointestinal system, e.g., by gastric fluid in the stomach. For example, the compositions can optionally be formulated to pass through the stomach unaltered and to dissolve in the intestines, i.e., as enteric-coated capsule or tablet compositions.

One of ordinary skill in the art would readily appreciate that the pharmaceutical compositions described herein can be prepared by applying known pharmaceutical manufacturing procedures as established through a long history of application for oral products. Such formulations can be administered to the subject with methods well-known in the pharmaceutical arts. Thus, the practice of the present methods will employ, unless otherwise indicated, conventional techniques of pharmaceutical sciences including pharmaceutical dosage form design, drug development, and pharmacology, as well as of organic chemistry, including polymer chemistry. Accordingly, these techniques are within the capabilities of one of ordinary skill in the art and are explained fully in the literature (see generally, for example, Remington: The Science and Practice of Pharmacy, Nineteenth Edition. Alfonso R. Gennaro (Ed.): Mack Publishing Co., Easton, Pa., (1995), hereinafter Remington, incorporated by reference herein in its entirety).

Methods of Treatment

According to various embodiments of the present invention, the compositions described herein can be administered to a subject to treat, which as described also includes reducing risk, preventing or reducing the rate of progression, reducing risk of progression and/or delaying development, of a disease susceptible to treatment by binding CD3. In some embodiments, the compositions are administered concurrently with one or more second therapeutic modalities as described herein.

EXAMPLES

Some embodiments of the present invention are further described in the following examples, which do not limit the scope of the invention described in the claims.

Example 1. Construction of Chimeric aCD3 IgG4 (Ser241Pro) mAb Containing Human CDRs from the Mouse FRs that were Mutated to De-Immunize the Molecule The VH and Vκ genes of murine OKT3 anti-CD3 mAb were synthesized using a series of overlapping oligonucleotides that were annealed, ligated and PCR-amplified to give full-length V regions. The sequences were derived from GenBank files A22261.1 and A22259.1 respectively. The assembled variants were cloned into the pANT expression vector system for IgG4 (Ser241Pro) VH chains (pANT-VhG4) and Vκ chains (pANTVκ). Both vectors contain genomic DNA fragments incorporating introns and poly-A sequences and an EBV OriP for enhanced transient expression in HEK/EBNA cells. Expression of both chains is driven by a CMV immediate early gene promoter (FIG. 1). The VH region was cloned using MluI and HindIII restriction sites, and the Vκ region was cloned using BssHII and BamHI restriction sites. All constructs were confirmed by sequencing.

Figure 2:
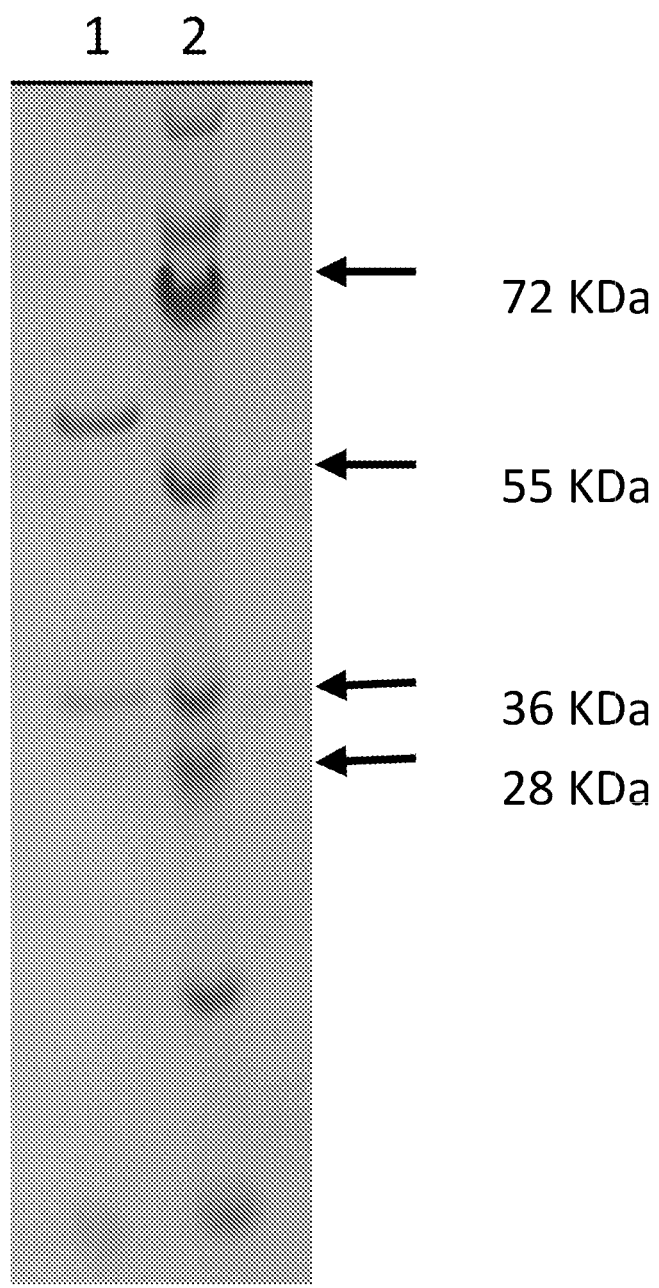
FIG. 2. SDS-PAGE profile of Chimeric anti-CD3 mAb. mAb (1 μg) was loaded on a NuPage 4-12% Bis-Tris gel (Invitrogen Cat. No. NP0322BOX), run at 200 V for 35 min, and stained with Coomassie Blue. Lane 1: Chimeric anti-CD3 mAb, Lane 2: Molecular size markers (prestained protein standard Fermentas PageRuler™, Cat. No. SM1811).

VH and Vκ plasmids were co-transfected into HEK/EBNA cells (ATCC Cat. No. CRL-10852) using linear PEI (Polysciences Cat. No. 23966-2). Following incubation for four days, supernatants were assayed for IgG levels using an IgG4 ELISA. Chimeric anti-CD3 mAb was purified from cell culture supernatants on a Protein A Sepharose column (GE Healthcare Cat. No. 110034-93) and buffer exchanged into phosphate-buffered saline (PBS) pH 7.4. Purified mAb was quantified by $OD_{280}$ using an extinction coefficient (Ec(0.1%)=1.62) based on its predicted amino acid sequence. Chimeric mAb was analyzed (FIG. 2) by sodium dodecyl sulfate polyacrylamide gel electrophoresis (SDS-PAGE). The murine anti-CD3 VL region joined to a human Cκ (region is glycosylated; the Vκ region terminates in 'N', and the first two residues of the human Cκ region are 'AS', thus adventitiously forming a 'NXS' glycosylation signal motif (the first two residues of murine Cκ are 'AK'). SDS-PAGE shows a minor band at the expected size of non-glycosylated L chain (28 kilodalton; kD), but most of the L chain appears to be glycosylated (36 kD).

Example 2. Design and Expression of Humanized V-Region Sequences

The objective was to generate fully humanized mAbs from the murine anti-CD3 OKT mAb (Orthoclone OKT3™, Janssen) by using Composite Human Antibody™ technology. The available OKT crystal structure in the RCSB Protein Data bank (accession no. 1SY6) was analyzed in order to identify important "constraining" amino acids in the V regions that are likely essential for the Ab binding properties. Residues contained within the CDRs (using both Kabat and Chothia definitions of CDRs) and some FR residues were considered important. VH and Vκ sequences of OKT (SEQ ID NOs: 15 and 16 respectively) contain typical FR residues, and the CDR 1, 2 and 3 motifs are comparable to many murine Abs. Thus, it was considered that composite human sequences of anti-CD3 mAb could be created with alternative amino acid sequences within FRs but with only a very small menu of possible alternative residues within the CDR. Preliminary analysis indicated that corresponding sequence segments from several human Abs could be combined to create CDRs similar or identical to those in the murine sequences with the goal of fully retaining the binding specificity of the anti-CD3 mAb. For regions outside of and flanking the CDRs, a wide selection of human sequence segments were identified as possible components of the novel composite human V regions.

Based on the above analysis, a large preliminary set of sequence segments that could be used to create composite human mAb variants was analyzed using iTope technology to evaluate peptide binding to human MHC class II alleles (Perry at al, Drugs in R&D 9: 385-96, 2008) and using the TCED™ for known antibody-related T-cell epitopes (Bryson et al, Biodrugs 24:1-8, 2010). Sequence segments that were identified as significant non-human germline binders to human MHC class II or that scored significant hits in TCED were discarded. This resulted in a reduced set of segments. Combinations of these were analyzed as above to ensure that the de-novo-created junctions between segments did not contain potential T-cell epitopes. Selected segments then were combined to produce VH and VL (Vκ) region sequences for synthesis. Three VH chains (VH1, VH2 and VH3, set forth in SEQ ID NOs: 9, 17 and 18) and three Vκ chains (Vκ1 Vκ2 Vκ3 set forth in SEQ ID NOs: 10, 19 and 20) were designed and are described in Table 1.

TABLE 1

New variant FRs according to Kabat numbering system

|     | FR1 | FR2 | FR3 | FR4 |
|-----|-----|-----|-----|-----|
| VH1 | QVQLVQSGSELKKP GASVKMSCKASGY TFT (SEQ ID NO: 21) | WVRQAPGKGLEWIG (SEQ ID NO: 22) | RATLTTDKSTSTAYM QLSSLRSEDTAVYYC AR (SEQ ID NO: 23) | WGQGTLVTVSS (SEQ ID NO: 24) |
| Vκ1 | QIVLTQSPATLSLSP GERATMSC (SEQ ID NO: 25) | WYQQKPGKAPKRWIY (SEQ ID NO: 26) | GVPSRFRGSGSGTDY TLTISSLQPEDFATYY C (SEQ ID NO: 27) | FGGGTKVEIK (SEQ ID NO: 28) |
| VH2 | QVQLVQSGSELKKP GASVKVSCKASGYT FT (SEQ ID NO: 29) | WVRQAPGKGLEWIG (SEQ ID NO: 30) | RATITTDKSTSTAYM ELSSLRSEDTAVYYC AR (SEQ ID NO: 31) | WGQGTLVTVSS (SEQ ID NO: 32) |
| Vκ2 | QIVLTQSPATLSLSP GERATLSC (SEQ ID NO: 33) | WYQQKPGKAPKRWIY (SEQ ID NO: 34) | GVPSRFSGSGSGTDY TLTISSLQPEDFATYY C (SEQ ID NO: 35) | FGGGTKVEIK (SEQ ID NO: 36) |

TABLE 1-continued

New variant FRs according to Kabat numbering system

| | FR1 | FR2 | FR3 | FR4 |
|---|---|---|---|---|
| VH3 | QVQLVQSGSELKKP GASVKVSCKASGYT FT (SEQ ID NO: 37) | WVRQAPGKGLEWIG (SEQ ID NO: 38) | RVTITTDKSTSTAYM ELSSLRSEDTAVYYC AR (SEQ ID NO: 39) | WGQGTLVTVSS (SEQ ID NO: 40) |
| Vκ3 | EIVLTQSPATLSLSP GERATLSC (SEQ ID NO: 41) | WYQQKPGKAPKRWIY (SEQ ID NO: 42) | GVPSRFSGSGSGTDY TLTISSLQPEDFATYY C (SEQ ID NO: 43) | FGGGTKVEIK (SEQ ID NO: 44) |

Underlined bolded residues in Table 1 represent mutations from the chimeric sequences as set forth in SEQ ID NOs: 7 (VH chain) and 8 (VL chain).

Although the amino acid sequences are described as "full sequences"; in fact the authentic leader sequences are not included, and common leader sequences are included in the vector. MGWSLILLFLVAVATRVHS (SEQ ID NO: 45) is the amino acid leader sequence for the H chain, and MRVPAQLLGLLLLWLPGARC (SEQ ID NO: 46) is the amino acid leader sequence for the κ chain. These are consensus mouse Ig leader sequences, i.e., they contain the most frequently used amino acids at each position from an alignment of known leaders from VH and Vκ genes respectively in the vectors to which the different variant DNA sequences were cloned.

For those sequences of IgG4 designated as "S241P", a mutation was made in the hinge region to change the Ser at position 241 to Pro. According to at least some embodiments of the present invention, humanized mAbs to CD3 comprise S241P.

Table 2 shows sequences of the CDRs as set forth in SEQ ID NOs: 1-6. VH-CDR1 (SEQ ID NO: 1), CDR2 (SEQ ID NO: 2 & CDR3 (SEQ ID NO: 3, mutated Cys100ASer in CDR3 is underlined) and VL-CDR1 (SEQ ID NO: 4), CDR2 (SEQ ID NO: 5) & CDR3 (SEQ ID NO: 6), according to at least some embodiments of the present invention.

TABLE 2

Sequences of CDRs, according to Kabat numbering system.

| Chain | CDR1 | CDR2 | CDR3 |
|---|---|---|---|
| VH | RYTMH (SEQ ID NO: 1) | YINPSRGYTNYNQKFKD (SEQ ID NO: 2) | YYDDHYSLDY (SEQ ID NO: 3) |
| VL | SASSSVSYMN (SEQ ID NO: 4) | DTSKLAS (SEQ ID NO: 5) | QQWSSNPFT (SEQ ID NO: 6) |

As noted above, there is a large preliminary set of sequence segments, including human germ-line FRs, that could be used to create composite human mAb variants. The use of large number of different FRs variants is to identify those that are less immunogenic using in-vitro tests and have properties such as binding and biological activity as close as possible to the original mouse OKT3 mAb, while recognizing that these properties cannot be predicted by any computer program.

All 6 variant composite human VH and Vκ region genes for anti-CD3 mAb, which can produce up to 3×3=9 humanized mAbs, were synthesized by means of overlapping oligonucleotides that were annealed, ligated and PCR-amplified to give full-length V regions. The assembled VH and Vκ regions were cloned into the pANT expression vector system for IgG4 (S241P) chains (FIG. 1, with new VH chains and Vκ regions) using MluI and HindIII restriction sites for the VH region and using BssHII and BamHI restriction sites for the Vκ region. All constructs were confirmed by sequencing. The nucleotide sequence of the VH chain in VH1/Vκ1Ser (SEQ ID NO: 13), which includes intron sequences (positions 359-576; 871-1262; 1299-1416; 1747-1843), is translated to the amino acid sequence shown in SEQ ID NO: 11, and the nucleotide sequence of the Vκ chain in VH1/Vκ1Ser (SEQ ID NO: 14), which includes a single intron sequence (positions 320-695), is translated to the amino acid sequence shown in SEQ ID NO: 12

All nine combinations of three IgG4 (Ser241Pro) VH and three Vκ chains (designated VH1/Vκ1, VH1/Vκ2, VH1/Vκ3, VH2/Vκ1, etc.) were co-transfected into HEK/EBNA cells using linear PEI (Polyethylenimine; Polysciences Inc.), then cells were incubated for 4 days. Supernatants with expressed mAbs were assayed for IgG levels using an IgG4 ELISA, mAbs were purified from supernatants on a Protein A Sepharose column and buffer exchanged into PBS pH 7.4. Purified Ab was quantified by $OD_{280}$ using an extinction coefficient (Ec(0.1%)=1.62)) based on predicted amino acid sequences. The variants were analyzed by SDS-PAGE; bands corresponding to the predicted sizes of the VH and Vκ chains were observed (FIG. 3).

Subsequently, additional VH2 variants in which Cys100A in CDR3 was mutated to Ala, Ser or Val were expressed in conjunction with Vκ2 and purified as above, and denoted VH2ser/Vκ1, VH2val/Vκ2, and VH2ser/Vκ3. These new CDR3-mutated mAb variants were tested for binding to Jurkat cells in order to identify the best CDR position 100A mutation in combination with one of the selected frameworks.

The ability of anti-CD3 mAb to bind to T cells is the required first step in exerting its therapeutic effects. Once mAb is bound to cells, the second step is for the mAb to provide a signal to T cells for modulating its immunological functions, i.e., stimulation of Tregs. Thus, the ability of anti-CD3 mAbs to bind to T cells (Example 3) as well as to provide a biological signal to T cells (Examples 4 & 5) w tested.

Example 3. Binding of Humanized mAbs to Human Cell-Surface CD3

Quantitative binding of anti-CD3 mAbs to human cell-surface CD3 was assessed by competition fluorescence-activated cell sorting (FACS) using human-CD3-surface-expressing Jurkat cells (ATCC Cat. #TIB-152) and commercially available OKT3-PE labeled conjugate (Abeam Cat. No. ab86882).

OKT3-PE was incubated in a range of concentrations with $3 \times 10^5$ Jurkat cells in FACS buffer (PBS pH 7.4, 1% BSA, 0.05% sodium azide). After incubating on ice, cells were washed, resuspended in 300 μL FACS buffer, and analyzed in a Becton Dickinson FACScalibur™. This preliminary study defined an $ED_{50}$ concentration (0.02 μg/mL) of OKT3-PE as giving the 50%-maximal signal in the assay. Based on this result, each Ab concentration in a dilution series (10 to 0.0006 μg/mL) of unlabeled CD3 mAb (OKT3) (eBiosciences™ Cat. No. 16-0037-85), Chimeric anti-CD3 mAb, negative control IgG1 ("Irr IgG1"), or humanized mAbs (FIG. 4A with VH2 variant mAbs differing at position 100A; and FIG. 4B with Ser100A or Cys100A variant mAbs) was mixed with a constant $ED_{50}$ concentration (0.02 μg/mL) of OKT3-PE and incubated on ice for 1 hr with 3×10⁵ Jurkat cells per dilution in FACS buffer. Cells then were washed and resuspended in 300 μL FACS buffer and analyzed on a Becton Dickinson FACScalibur™.

Binding of OKT3-PE to Jurkat cells was assessed by incubating a dilution series of the Ab (1.0 to 0.0005 μg/mL) with Jurkat cells as noted (FIG. 4 legend). The $ED_{50}$ (effective concentration for stimulating 50% of the maximal fluorescence signal) for OKT3-PE was calculated in this preliminary experiment (0.02 μg/mL) and used in subsequent competition binding studies. Dilutions of mAb variants competed against the $ED_{50}$ of OKT3-PE for binding to Jurkat cells and displacing the fluorescence signal. VH2 CDR3-mutated variants were tested relative to Cys100A parental CDR3 in conjugation to Vκ1-3 (FIG. 4A). The calculated $IC_{50}$ values (Table 3) show that VH2ser/Vκ2 mutant showed slightly improved competition compared to VH2ala/Vκ2 mutant and both of these were significantly better than VH2val/Vκ2 mutant. The VH2ser/Vκ2 mutant was also slightly improved compared to the original VH2cys/Vκ2 variant. This ranking of the mutation of Cys100A to Ala, Ser and Val was consistently observed in a number of experiments. Thus, Cys100A to Ser was selected as the preferred mutation.

TABLE 3

Calculated $IC_{50}$ values for VH2 mutants (Cys100A to Ala, Ser and Val).

| Construct | IC50 (ng/mL) |
|---|---|
| Chimeric | 37 |
| OKT3 | 35 |
| VH2cys/Vκ2 | 45 |
| VH2ala/Vκ2 | 45 |
| VH2ser/Vκ2 | 41 |
| VH2val/Vκ2 | 55 |

Based on activity in biological assays (Examples 4 & 5), selected Cys100A mutant mAbs (VH1ser/Vκ1, VH1ser/Vκ2, VH2ser/Vκ2, VH2ser/Vκ3) were tested in the competition binding assay along with the corresponding parental Cys100A mAbs. The mAbs tested gave similar binding in this assay (FIG. 4B).

Figure 5A:
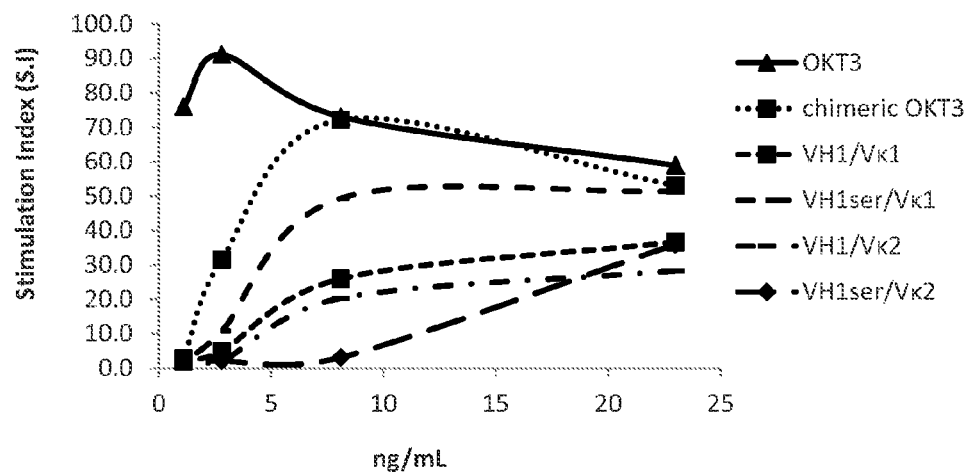
FIGS. 5A and 5B. T-cell proliferation assay of humanized MAbs. Dilutions of OKT3 mAb, Chimeric anti-CD3 mAb and humanized mAbs were incubated with peripheral blood mononuclear cells (PBMC) for 2 days at 37° C., then ³H-Thymidine (1 μCi) was added overnight. Cells were harvested, and cpm were measured by β-counter. Stimulation index (SI) was calculated as (sample cpm/medium-alone cpm). (A) the humanized variants VH1/Vκ1 and VH1/Vκ2 were tested with Cys or Ser residue at position 100A; and (B) the variants VH2/Vκ2 and VH2Vκ3 having Cys or Ser residue at position 100A were tested.
Figure 5B:
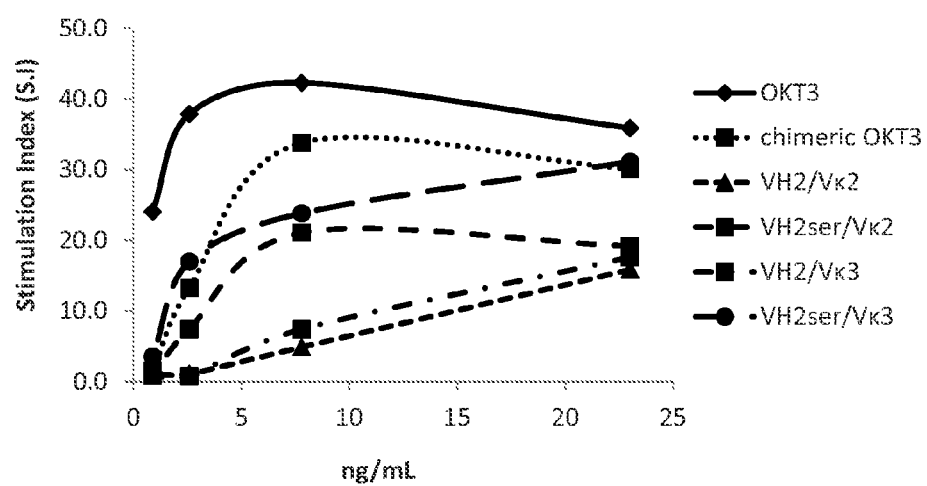

Example 4. Biological Activity 1; Signaling of T-Cell Proliferative Activity by Humanized mAbs Following cell binding, anti-CD3 mAb exerts its biological activity for stimulating immunological effector functions through signals to T cells for stimulating Tregs. The capacity of novel anti-CD3 mAbs to support T-cell proliferation and cellular signaling was evaluated using PBMC. Proliferative assays were conducted to evaluate the VH1/Vκ1, VH1/Vκ2, VH2/Vκ1, VH1/Vκ1 and VH2Vκ3 FR variant mAbs with or without the Cys100ASer mutant. Proliferative activities of the humanized anti-CD3 mAbs (having Cys100A) were compared at different concentrations to those of the Chimeric mAb and OKT3 mAb, with stimulation index (SI) plotted against Ab concentration (FIG. 5) in order to identify the best-performing VH/Vκ combination into which to insert the Cys100ASer mutation. In each case of the four FRs, the Cys100ASer mutant unexpectedly showed increased proliferative activity as reflected in higher SI relative to the parent mAb. Of the FRs tested, two different FRs containing the Cys100ASer mutation, VH1ser/Vκ1 and VH2ser/Vκ3 showed similar proliferative activity to that of the Chimeric mAb, while the other two FRs tested with or without the Cys100ASer mutation show much lower proliferative activity (FIGS. 5A & B).

Example 5. Biological Activity 2; Signaling of IL-2 Secretion by Humanized mAbs

The cellular signaling activity of humanized anti-CD3 mAbs toward stimulating immunological effector functions was further evaluated by the ability of the four FR variants VH1ser/Vκ1, VH1ser/Vκ2, VH2ser/Vκ2, and VH2ser/Vκ3 (all having the Cys100ASer mutation) to stimulate IL-2 secretion by Jurkat cells. Dynabead® M-450 beads (Invitrogen cat. no. 140.13) were coated overnight with 2 μg test mAb plus 4 μg anti-CD28 Ab (Abeam cat. no. ab85986), washed, and incubated at three different bead:cell ratios (2:1, 3:1 and 4:1) with 1×10⁵ Jurkat cells for 16 hr at 37° C. Culture supernatants were diluted 1:1 and assayed for IL-2 concentration using eBiosciences™ IL-2 ELISA kit (cat. no. 88-7025).

Figure 6:
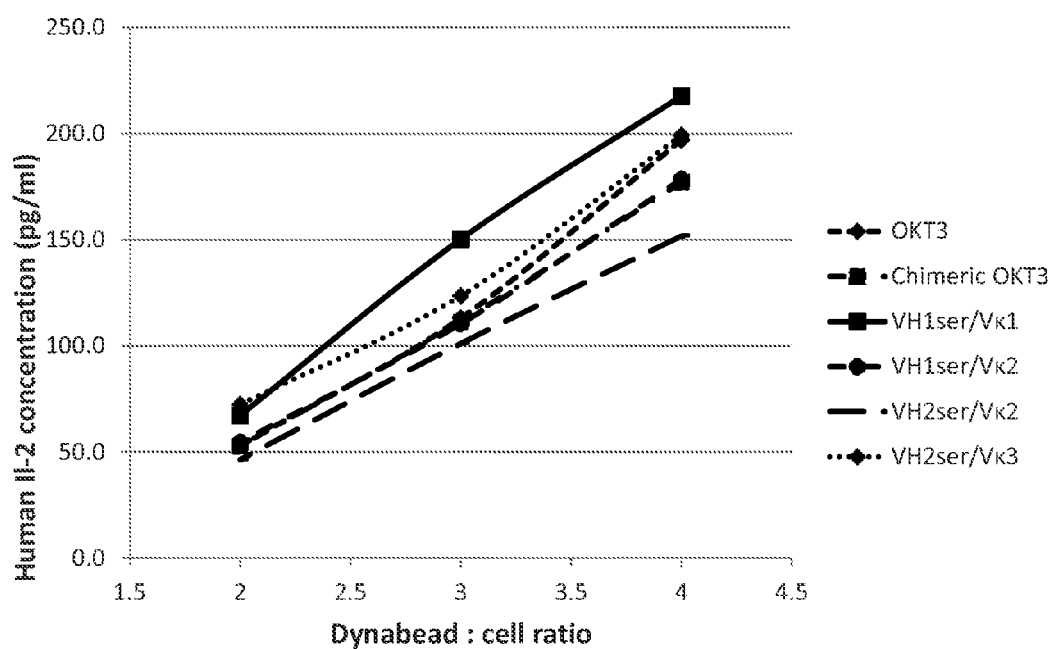
FIG. 6. IL-2 secretion assay of selected humanized mutants. The ability of the four different FR variants VH1ser/Vκ1, VH1ser/Vκ2, VH2ser/Vκ2, and VH2ser/Vκ3, and Orthoclone OKT3™ and Chimeric anti-CD3, to stimulate IL-2 secretion by Jurkat cells was assayed with Dynabead® M-450 beads coated with the tested mAb anti-CD28. IL-2 concentrations were measured using eBioscience IL-2 ELISA kit.

The similar levels of IL-2 secretion in response to OKT3, Chimeric anti-CD3, and VH1/Vκ1 mAbs reflected similar signaling activity. The VH1ser/Vκ2, VH2ser/Vκ2 and VH2ser/Vκ3 FR variants stimulate IL-2 secretion to levels (~50-180 pg/mL) below or similar to that of the Chimeric anti-CD3. Unexpectedly, VH1ser/Vκ1 FR variant mAb stimulated a response well above those of other FR variant mAbs and stronger than the responses for OKT3 mAb and Chimeric anti-CD3 mAb, reaching a peak of 218 pg/mL (FIG. 6). Therefore, there is a clear advantage in biological signaling activity to the VH1ser/Vκ1 mAb over the other FR variant mAbs, over Chimeric anti-CD3 mAb, and over OKT3 mAb, while it retains its full binding capacity and specificity for CD3.

Example 6. Stability Study—Comparison of the Stability of VH1ser/Vκ1, VH2ser/Vκ3 and OKT3

Differences in stability among anti-human-CD3 FR variant mAbs were evaluated by exposing the mAbs to high temperature and evaluating aggregation by dynamic light scattering (DLS). VH1ser/Vκ1, VH2ser/Vκ3 and Orthoclone OKT3™ (control, Orthoclone, Muromab mouse anti-human-CD3, Janssen-Cilag Ltd, Raritan, N.J., USA) mAbs were subjected to accelerated stability testing by incubating them at a concentration of 1 mg/mL for 5 minutes in a UV-microcuvette (70 μL/microcurvette, BRAND GMBH™, Wertheim, Germany) at temperatures from 20 to 75° C. in 5-10° C. intervals. Aggregation was evaluated at each temperature by five measurements of Z-average size of particle diameter in nm on a Zetasizer Nano-SZ™ nanoseries instrument (Malvern instruments Ltd. Worcestershire, UK). In samples that contained multiple particles, the bar represents the most intense peak volume that is >90% of all particles in sample. Analysis was performed with Zetasizer™ software 7.01 (Malvern Instruments Ltd, Worcestershire, UK).

Figure 7:
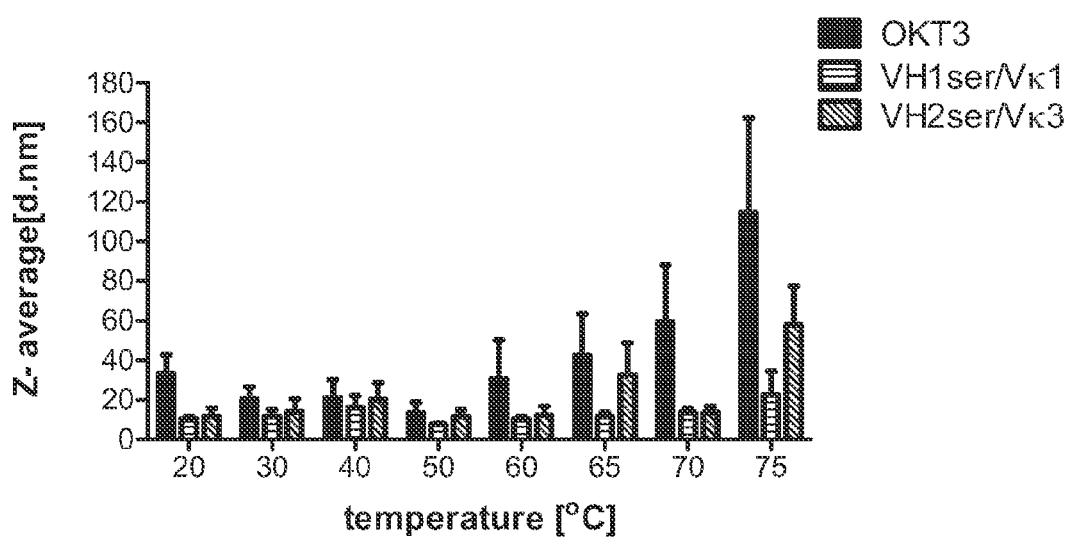
FIG. 7. Stability study—comparison between humanized variant mAbs and OKT. Aggregation of the variant humanized mAbs VH1ser/Vκ1 and VH2ser/Vκ3 and control murine Orthoclone OKT3™ (Muromab mouse anti-human-CD3, Janssen-Cilag Ltd, Raritan, N.J., USA) was tested from 20 to 75° C., by measuring Z-average size of particle diameter on a Zetasizer Nano-SZ™, nanoseries instrument (Malvern instruments Ltd. Worcestershire, UK). In samples that contained multiple particles, the bar represents the most intense peak volume that is >90% of all particles in sample.

The data show that VH1ser/Vκ1 unfolds and aggregates at a higher temperature than does either VH2ser/Vκ3 and OKT3 mAbs (FIG. 7), where such performance at higher temperature indicates superior stability. The higher transition temperatures in the context of humanized FRs are a function of the different FR variants and the parental OKT3 mAb. The humanized de-immunized VH1ser/Vκ1 is different from VH2ser/Vκ3 in only few amino acids of their FRs but unexpectedly has increased stability at all measured temperatures, including increased stability compared to the original murine OKT3 mAb. Better stability gives VH1ser/Vκ1 a pharmaceutical and commercial advantage over the other variants in terms of pharmaceutical properties.

Example 7. Stability of VH1ser/Vκ1 Versus its Parental mAb VH1 Cys/Vκ1

VH1ser/Vκ1 (VH1s) and VH1cys/Vκ1 (VH1c) mAbs were dialyzed into 20 mM citrate phosphate buffer to concentrations of 0.15-0.20 mg/mL, then evaluated spectroscopically across the range of pH 3-8 at pHs 5 and 7. Far-UV circular dichroism (CD) measurements were performed using an Applied Photophysics Chirascan Plus Spectrophotometer (Leatherhead, UK) equipped with a Peltier temperature controller. Complete spectra were collected at 1.25° C. intervals at a temperature ramp rate of 1° C./min and 60 sec incubation from 10 to 87.5° C. in the wavelength range of 195-260 nm. An averaging time of 0.5 s/nm, a 1-nm bandwidth, and a 60-sec setting time were used. A 0.1-cm path-length quartz cuvette (Sterna) sealed with a Teflon stopper was used for acquiring CD spectra. The data were analyzed using Orgin (V7.0) software.

A PTI QM-1 spectrofluorometer (Brunswick, N.J.) equipped with a four-position Peltier temperature-controlled cell-holder and 1-cm path-length cuvette were used to quantify intrinsic fluorescence and light scattering, without applying inner filter corrections. An excitation wavelength of 295 nm was used for simultaneously measuring light scattering and intrinsic tryptophan fluorescence. Emission spectra were collected over a range of 305-405 nm at a 1 nm/s collection rate. A second photomultiplier placed at 180° to the emission detector was used to record light scattering. Spectra were collected at 2.5° C. intervals over the range of 10-87.5° C. with a 3-min equilibration at each temperature. Fluorescence intensity and peak positions were obtained by a mean spectrum-mass method, subsequent to buffer subtraction. Data analysis was performed using Felix (PTI) and Origin (V7.0) software. All spectroscopic data were assembled into Empirical Phase Diagrams (Maddux et al, J Pharm Sci, Jun. 6, 2011).

Figure 8A:
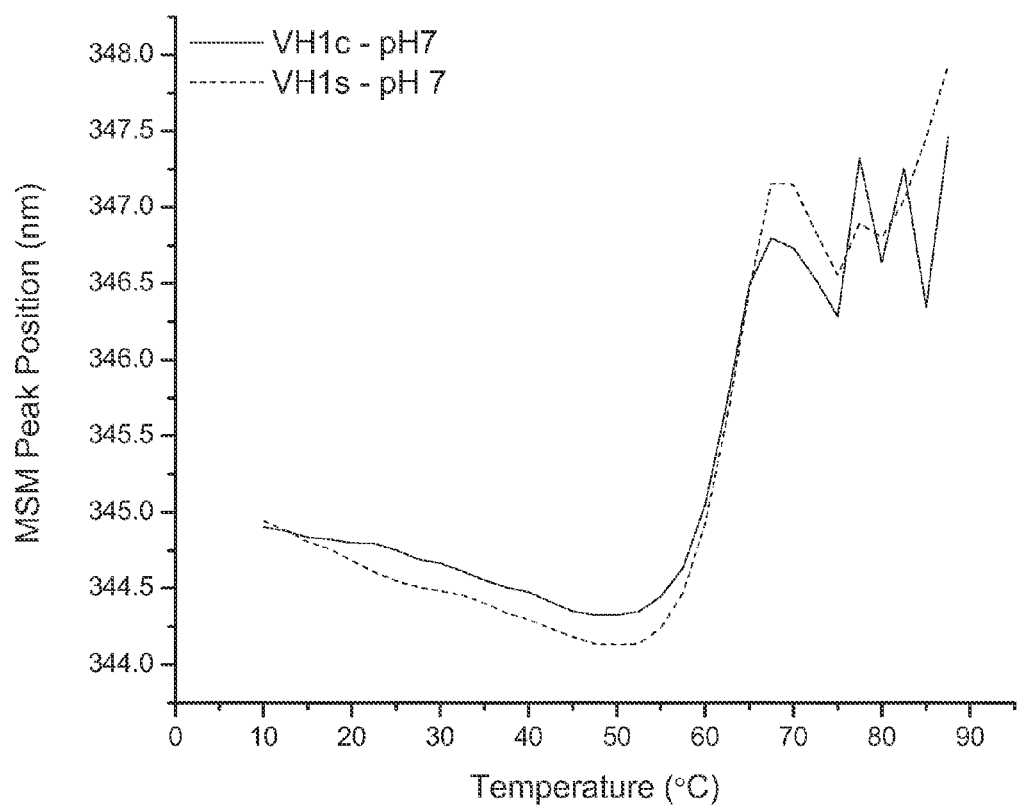
FIGS. 8A-8C. Spectroscopic analyses of mAbs at pH7. Mean spectral mass peak position (A) and intensity (B) obtained from intrinsic fluorescence experiments and from light scattering (C) were quantified at pH7 as a function of temperature from 10 to 87.5° C. Data are shown for VH1cys/Vκ1 (solid lines) and VH1ser/Vκ1 (dotted lines).
Figure 8B:
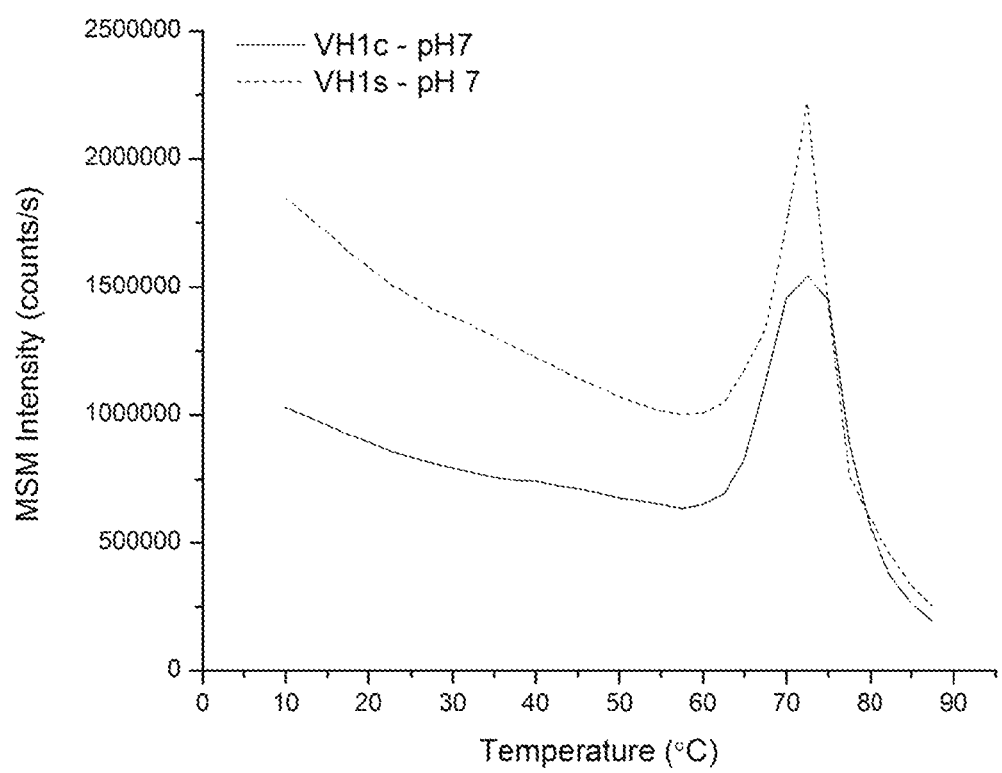
Figure 8C:
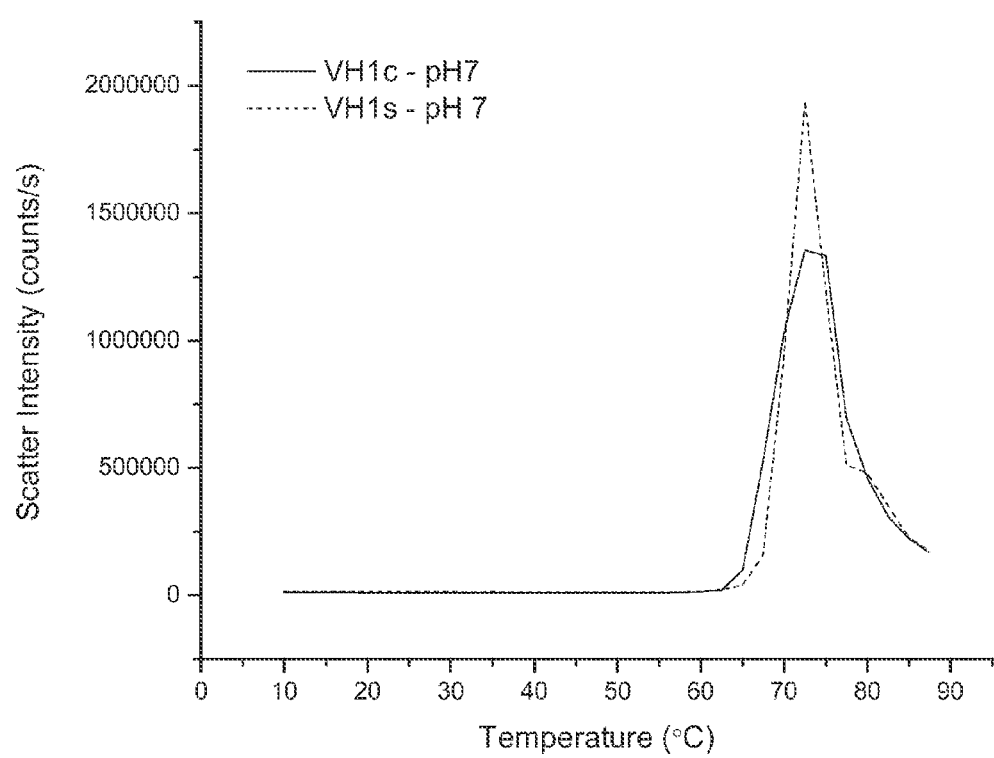
Figure 9A:
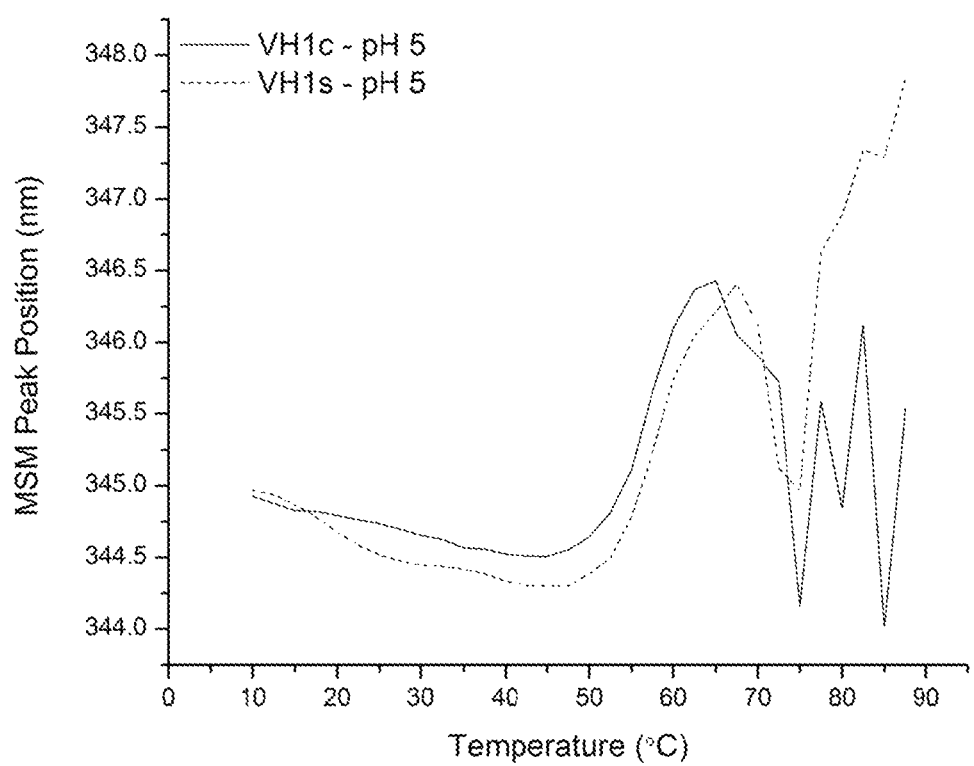

Mean spectral mass peak position (a) and intensity (b) obtained from intrinsic fluorescence experiments and light scattering (c) as a function of temperature from 10-87.5° C. are shown at pH7 (FIG. 8) and pH5 (FIG. 9) for VH1cys/Vκ1 mAb (solid lines) and VH1ser/Vκ1 mAb (dotted lines). The melting and onset temperatures from these spectroscopic analyses are summarized in Table 4.

TABLE 4

Melting and onset temperatures[1] for VH1ser/Vκ1 and VH1cys/Vκ1 mAbs

| mAb | pH | MSM Peak Position[2] | | MSM Intensity[2] | | Light Scattering | |
|---|---|---|---|---|---|---|---|
| | | Tonset | Tm | Tonset | Tm | Tonset | Tm |
| VH1s | 5 | 52.6 | 62.3 | 55.5 | 67.1 | 67.3 | 67.8 |
| | 7 | 57.2 | 63.5 | 54.8 | 68.9 | 67.1 | 69.7 |
| VH1c | 5 | 51.1 | 57.5 | 47.7 | 63.1 | 64.6 | 66.9 |
| | 7 | 55.8 | 62.5 | 57.6 | 67.1 | 64.4 | 68.4 |

[1]Uncertainties of values are estimated at ±5° C.
[2]Calculated from the mean spectral mass of the fluorescence spectra.

These data show that VH1 ser/Vκ1 unfolds and aggregates at a clearly higher temperature than does VH1cys/Vκ1. The higher transition temperatures for VH1ser/Vκ1 indicate an overall unexpected increase in stability relative to VH1cys/Vκ1 in terms of better maintenance of the Ig structure under the stress of temperature. VH1ser/Vκ1 is further useful in that the elimination of the unpaired Cys100A residue in CDR3, which unexpectedly increased T-cell signaling activities relative to both Chimeric anti-CD3 mAb and OKT3 mAb while not reducing T-cell-surface binding, obviates inappropriate disulfide bond formation, thus enhancing the pharmaceutical stability of the VH1 ser/Vκ1 mAb.

Thus, the analyses detailed in Examples 4-7 have shown the following.

VH1ser/Vκ1 mAb, with a Cys100ASer point mutation in the context of humanized FRs relative to its parental mAb molecule, is a humanized de-immunized anti-CD3 variant mAb that, unexpectedly, has shown increased stability and increased T-cell signaling toward stimulating immunological effector functions in both T-cell proliferation and IL-2 secretion relative to its VH1cys/Vκ1 parent mAb, and functional activities that are similar to or superior than the Chimera anti-CD3 mAb, and similar to or better than the original murine OKT3 mAb. Furthermore, VH1ser/Vκ1 mAb has unexpectedly better stability and superior biological signaling for IL-2 secretion than another humanized variant VH2ser/Vκ3 mAb even though there are only a few differences in their amino acid sequences, thus reinforcing the unexpectedly superior properties of VH1ser/Vκ1 mAb given that none of these properties could have been predicted by the amino acid sequences of the mAbs.

It is well known in the art that the humanization process usually reduces the binding and/or activity and/or stability of the humanized variant mAb relative to its parent mAb (as was the case for most of the tested variant anti-CD3 mAbs). These results show that the Cys100ASer point mutation is not inferior in binding and unexpectedly is stronger in signaling activity and in pharmaceutical stability relative to its original parental Chimeric mAb and mouse OKT3 mAb. These non-obvious results provide for a mAb with improved utility for clinical and pharmaceutical development.

Example 8. Ex-Vivo Analysis of Immunogenicity of Humanized FRs Variant mAbs

EpiScreen™ technology is an ex vivo assay that quantifies T-cell responses to protein therapeutics, including mAbs, for the potential to induce an immune response (Jones et al, J Interferon Cytokine Res 24: 560-72, 2004. Jones et al, J Thromb Haemost 3: 991-1000, 2005), in particular for a humanized mAb to induce HAHA. Previous EpiScreen™ assays with a range of biologics have shown a clear correlation between the percentage of T-cell responses in the assay and the level of immunogenicity and HAHA/

HAMA (antibody response to the therapeutic protein or mAb) observed in the clinic (Perry L C et al, Drugs R&D, 9: 385-96, 2008).

PBMCs were isolated from buffy coats (from blood drawn within 24 hr of assay) of healthy community donors by Lymphoprep (Axis-shield, Dundee, UK) density centrifugation, and CD8+ T cells were depleted using CD8+ RosetteSep™ (StemCell Technologies Inc, London, UK). Donors were characterized by identifying HLA-DR allotypes using a tissue-typing kit (Biotest, Solihull, UK). T-cell responses to control antigens (e.g., KLH) and control peptides derived from Influenza A and Epstein-Barr viruses also were determined. PBMCs were frozen and stored in liquid nitrogen until required. A cohort of 21 donors was selected (Table 5) to best represent the number and frequency of HLA-DR allotypes expressed in the world population, and thus be useful to screen for the potential to elicit HAHA responses in a human subject. Analysis of the allotypes expressed in the cohort against those expressed in the world population revealed that all major HLA-DR alleles (individual allotypes with a frequency >5% expressed in the world's population) were well represented.

TABLE 5

Donor haplotypes. HLA-DR typing is shown for each of the 21 donors

| Donor No | Haplotype |
|---|---|
| 1 | DRB1*15, DRB1*16; DRB5* |
| 2 | DRB1*03, DRB1*04; DRB3*; DRB4* |
| 3 | DRB1*03, DRB1*15; DRB3*; DRB5* |
| 4 | DRB1*03; DRB3*; DRB4* |
| 5 | DRB1*07, DRB1*08; DRB4* |
| 6 | DRB1*07, DRB1*15; DRB4* |
| 7 | DRB1*12, DRB1*13; DRB4*; DRB5* |
| 8 | DRB1*13, DRB1*15; DRB3*; DRB5* |
| 9 | DRB1*12, DRB1*13; DRB3* |
| 10 | DRB1*04, DRB1*07; DRB3*; DRB4*; DRB5* |
| 11 | DRB1*13; DRB3*; DRB4* |
| 12 | DRB1*01; DRB4* |
| 13 | DRB1*04, DRB1*07; DRB4* |
| 14 | DRB1*04, DRB1*13, DRB3*DRB4* |
| 15 | DRB1*01, DRB1*04; DRB4* |
| 16 | DRB1*04; DRB4* |
| 17 | DRB1*15, DRB1*07; DRB4*; DRB5* |
| 18 | DRB1*15, DRB1*04; DRB4*; DRB5* |
| 19 | DRB1*04, DRB*12; DRB3*; DRB4* |
| 20 | DRB1*10, DRB1*13, DRB3*, DRB4* |
| 21 | DRB1*09, DRB1*11, DRB3*, DRB4* |

PBMCs from each donor were revived in culture medium, and dendritic cells (DCs) were isolated using Miltenyi Monocyte Isolation kit II and LS columns (Miltenyi Biotech, Oxford, UK). Monocytes were resuspended in culture media to 4-6×10⁶ cells/mL and distributed in 24-well plates (2 mL final volume per well). Cells were washed on Day 3 and resuspended in culture medium. Purified VH1ser/Vκ1 mAb and Chimeric anti-CD3 mAb (25 µg/mL) were added to cells, and an equivalent volume of culture medium was added to untreated control wells. DCs were incubated with mAb or control medium for 24 hr, after which cells were washed and resuspended in culture medium containing 50 ng/mL TNFα (Peprotech) in order to mature the cells. DCs were harvested on Day 8 and counted, and viability was assessed using trypan blue dye exclusion. DCs then were γ-irradiated (4000 rads) before use in the proliferation assays. Autologous CD4+ T cells were isolated by negative selection from frozen PBMCs using CD4+ T Cell Isolation Kit II (Miltenyi Biotech). After counting and assessing cell viability, 1×10⁵ CD4+ T cells were added to 1×10⁴ DCs in 96-well round bottom plates. A set of wells containing PHA was included as positive control for each donor. All samples were tested in sextuplicate cultures. Cells were cultured for 7 days, pulsed with 1.0 µCi³H-thymidine (Perkin-Elmer, Beaconsfield, UK), incubated for 6 hr and harvested onto filter mats using a TomTec Mach III cell harvester. Counts per minute for each well were determined by Meltilex (Perkin-Elmer) scintillation counting on a Microplate Beta Counter. For proliferation assays, samples inducing proliferative responses higher than a threshold stimulation index (SI≥2.0) are deemed positive. For proliferation data in a set of sextuplicate assays, a positive response is defined by a statistical threshold, where significance (p<0.05) of the response is assessed by comparing cpm of test wells against cpm of control wells using unpaired two-sample student's t-test.

VH1 ser/Vκ1 mAb did not induce any positive responses in the proliferation assay according to the SI≥2.0 threshold in any of the 21 donor T-cell populations, whereas the Chimeric mAb induced proliferation responses in 19% of donors. All donor cells responded strongly to the PHA positive control, indicating that T cells for each donor were responsive to stimulation (Table 6). These data show that humanized VH1ser/Vκ1 mAb has very low or no potential clinical immunogenicity for a HAHA response and thus has been successfully de-immunized, while the Chimeric anti-CD3 and by inference its OKT3 mAb parent has significant immunogenic potential for eliciting a HAHA response. Indeed, oral administration of OKT3 anti-CD3 mAb in Phase 2a clinical trials was shown to be immunogenic in that HAMA responses were detected (Example 9).

TABLE 6

Summary of cell proliferation. "P" = positive proliferation responses (SI ≥ 2.0, p < .05). The frequency of responses to each mAb or PHA positive control in T cells for the cohort of 21 donors is shown as a percentage.

| | Chimeric | VH1s/VK1 | PHA |
|---|---|---|---|
| Donor 1 | | | P |
| Donor 2 | P | | P |
| Donor 3 | | | P |
| Donor 4 | | | P |
| Donor 5 | | | P |
| Donor 6 | | | P |
| Donor 7 | | | P |
| Donor 8 | P | | P |
| Donor 9 | | | P |
| Donor 10 | | | P |
| Donor 11 | | | P |
| Donor 12 | P | | P |
| Donor 13 | P | | P |
| Donor 14 | | | P |
| Donor 15 | | | P |
| Donor 16 | | | P |
| Donor 17 | | | P |
| Donor 18 | | | P |
| Donor 19 | | | P |
| Donor 20 | | | P |
| Donor 21 | | | P |
| Proliferation % | 19 | 0 | 100 |

Example 9. In Silico Analysis of Anti-CD3 V Region Sequences of Subject Inventive mAb and Teplizumab The VH1ser/Vκ1 mAb (an exemplary mAb described in Example 2) is a noteworthy improvement over teplizumab, a known humanized anti-CD3 mAb, as noted in the current analysis. Software known as iTope™ (Perry et al, Drugs in R&D 29: 385-96, 2008) was used to assess overlapping peptides from teplizumab (SEQ ID NO: 47 and SEQ ID NO: 48) and VH1ser/Vκ1 mAb (SEQ ID NO: 9 and 10) V region sequences for promiscuous high-affinity binders to human MHC class II. The teplizumab sequence was taken from US Application No. 20070077246; this sequence was stated to be advantageous in that the resultant Ab has ≥50% reduced binding to at least one FcγR than an Ab with a wild-type Fc domain By contrast, the subject inventive VH1s/Vκ1 mAb features a wild-type Fc domain that does not have reduced binding to FcγR.

Promiscuous high-affinity MHC class II binding peptides are thought to correlate with the presence of T-cell epitopes (Hill et al, Arthritis Res Ther 1: R40-8, 2003), although medium and low-affinity binders can also trigger T-cell responses. Thus iTope™ was used to provide a useful initial "low resolution" screen for the location of potential T-cell epitopes to design asset of peptides for EpiScreen™ T-cell epitope mapping. In addition, the sequences were also analyzed by TCED™ (Bryson et al, Biodrugs 24:1-8, 2010; EP2080138 and related) BLAST search to locate any T-cell epitopes previously identified by EpiScreen™ analysis of other protein sequences.

The iTope™ software predicts favorable interactions between amino acid side chains of a peptide and specific binding pockets (in particular pocket positions; p1, p4, p6, p7 and p9) within the binding grooves of 34 human MHC class II alleles. The location of key binding residues is achieved by the in silico generation of 9-mer peptides that overlap by one amino acid spanning the test protein sequence. Comparisons with physical MHC class II binding experiments have shown that iTope™ can successfully discriminate with high accuracy between peptides that either bind or do not bind MHC class II molecules. The results should be assessed in light of predictive methods for MHC class II binding over-predicting the number of T-cell epitopes since they do not allow for other processes during antigen presentation such as protein/peptide processing, recognition by the T-cell receptor, or T-cell tolerance to the peptide. The TCED™ contains the sequences of all the peptides previously screened in EpiScreen™ T cell epitope mapping assays. The TCED™ is used to search any test sequence against a large (>10,000 peptides) database of peptides derived from unrelated protein and antibody sequences which have been tested in EpiScreen™ T cell epitope mapping assays.

Analysis of the teplizumab VH and VL regions (SEQ ID NO: 47 and 48) and VH1ser/Vκ1 (SEQ ID NO: 9 and 10) sequences using iTope™ was performed with overlapping 9-mers spanning the variable regions, which were tested against each of the 34 MHC class II allotypes. Each 9-mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e., 17 out of 34 alleles) had a high binding affinity (score >0.6), such peptides were scored as "promiscuous high-affinity" MHC class II binding peptides, which are considered a high risk for containing CD4+ T-cell epitopes. Promiscuous moderate-affinity MHC class II binding peptides bind >50% of alleles with a binding score >0.55. Further analysis of the sequences was performed using the TCED™. The sequences were used to interrogate the TCED™ by BLAST search in order to identify any high sequence homology between peptides (T-cell epitopes) from unrelated proteins/antibodies that stimulated T-cell responses in previous EpiScreen™ studies.

Data for iTope™ and TCED™ analyses (Table 7) show that the tepilizumab VH sequence was found to contain two non-germline promiscuous moderate-affinity MHC class II binding sequences with each 9-mer beginning at residues V2 and W36. In addition, the peptide beginning at L86 was found to be a perfect match to a positive peptide in the TCED™; this is a confirmed T-cell epitope. The VH and Vκ sequences of VH1ser/Vκ1 (SEQ ID NO: 9 and 10) contained no non-germline promiscuous MHC class II binding sequences and gave no TCED™ hits.

The tepilizumab Vκ sequence was found to contain four promiscuous non-germline high-affinity MHC class II binding peptides and one promiscuous non-germline moderate-affinity MHC class II binding sequences. The high-affinity peptide 9-mers begin at residues I2, V3, V19 and F61, and the moderate affinity peptide begins at residue L4. The peptide beginning at I74 also is a partial match to a positive peptide in the TCED™, with 7 of 9 amino acids being identical and matching at 4 of 5 key binding positions. The Vκ sequence of VH1ser/Vκ1 (SEQ ID NO:10) contained no non-germline promiscuous MHC class II binding sequences and gave no TCED™ hits.

On the basis of these results, particularly with the confirmed and partially matched T-cell epitope from the TCED™ analysis and the numbers of non-germline promiscuous MHC class II binding peptides, one would expect tepilizumab to have significant risk for immunogenicity in eliciting HAHA responses, while the VH1ser/Vκ1 mAb would be expected to have no significant risk of eliciting HAHA responses upon administration to human subjects by the oral or other route. The data summarized in Example 8 highlight the importance of avoiding immunogenicity of the mAb, since a HAHA response against the therapeutic mAb can interfere with its clinical efficacy or cause undesirable clinical immunological side effects, as is well known in the art. In this sense, the VH1ser/Vκ1 mAb is clearly preferred over tepilizumab for oral administration to prevent or treat inflammatory or autoimmune diseases as described herein.

TABLE 7

Summary of iTope ™ and TCED ™ analysis of tepilizumab and VH1ser/Vκ1.

|  | iTope ™ PHA | iTope ™ PMA | TCED ™ |
| --- | --- | --- | --- |
| tepilizumab VH | 0 | 2 | 1 |
| tepilizumab Vκ | 4 | 1 | 1 |
| VH1 of VH1ser/Vκ1 | 0 | 0 | 0 |
| VκI of VH1ser/Vκ1 | 0 | 0 | 0 |

PHA: promiscuous high-affinity MHC class II binding peptides,
PMA: promiscuous moderate-affinity MHC class II binding peptides.

It is well known in the art that the humanization process usually reduces the binding and/or activity and/or stability of the humanized variant mAb relative to its parent mAb (as was the case for most of the tested variant anti-CD3 mAbs) (Foote J and Winter G. J Mol Biol 224: 487, 1992; and US Patent Application No. 20080206239, Jones T et al). These results show that the VH1ser/Vκ1 FR is not inferior in binding and unexpectedly is stronger in signaling activity and more stable relative to its original parental Chimeric mAb and mouse OKT3 mAb. Together with the observed increased T-cell signaling toward stimulating immunological effector functions in both T-cell proliferation and IL-2 secretion the present results provides a non-obvious phenomena and a mAb with improved utility for clinical and pharmaceutical development.

Example 10. Treatment with OKT3 mAb of Subjects with NASH or Hepatitis C

A Phase 2a clinical trial was conducted in subjects with NASH and the metabolic syndrome, in which groups of nine subjects received one of three OKT3 anti-CD3 mAb dosage levels (o.2, 1.0 or 5.0 mg) or placebo once daily for 30 days. Subjects also received one 20 mg dose of omeprazole, a proton-pump inhibitor, for enhancing the gastric stability of the mAb. Oral anti-CD3 MAb immunotherapy was found to be safe and well-tolerated, and induced positive statistical trends in clinical biomarkers and immunological markers in groups receiving OKT3 anti-CD3 MAb but not in the placebo group; some of these trends were statistically significant in spite of the very small group sizes. These positive clinical biomarker effects were reduced blood levels of two enzymes (ALT, AST) that are biomarkers for liver inflammation which is a favorable outcome for subjects with NASH, and reduced blood levels of glucose and triglycerides and improved performance in glucose tolerance testing which is a favorable outcome for subjects with type-2 diabetes or altered glucose metabolism or the metabolic syndrome. Favorable changes also were observed in immunological markers consistent with the induction of Tregs and of anti-inflammatory immune responses, and correlations were found between some favorable immunological changes and clinical biomarker changes.

A second Phase 2a clinical trial with the same trial design and size as the above Phase 2a NASH study was conducted in subjects with chronic hepatitis C. Oral OKT3 anti-CD3 mAb immunotherapy was found to be safe and well-tolerated, and induced positive trends in clinical biomarkers and immunological markers in groups receiving OKT3 but not in the placebo group; some of these trends also were statistically significant. These positive effects were reduced blood levels of two enzymes (ALT, AST) that are biomarkers for liver inflammation and reduced levels of hepatitis C virus, both of which are favorable outcomes for subjects with chronic hepatitis C. Favorable changes also were observed in immunological markers consistent with the induction of Tregs and of anti-inflammatory immune responses, and correlations were found between some favorable immunological changes and clinical biomarker changes.

In both Phase 2a clinical trials, HAMA responses were observed in some OKT3 mAb-treated subjects but not in placebo-treated subjects, indicating that the OKT3 mAb is immunogenic, and sustained oral immunotherapy with an immunogenic mAb may induce Ab that can reduce efficacy of oral mAb immunotherapy or induce undesirable side effects. These unexpected HAMA data show that it is desirable to create and develop a de-immunized humanized mAb, as in the case of the subject mAb, in order to obviate potential HAHA responses.

Example 11. Treatment of Subject with NASH with VH1ser/Vκ1 mAb

Efficacy of VH1ser/Vκ1 mAb (an exemplary mAb described in Example 2) is assessed in a clinical trial of patients with some symptoms of NASH. Optionally, patients having one or more markers of NASH but who are otherwise pre-symptomatic are evaluated. The patients receive doses of VH1ser/Vκ1 mAb over, e.g., a 6-month interval or longer at a dosing frequency of, e.g., daily to weekly, administered as a liquid solution, at dosage levels of, e.g., 0 (placebo group), 1, and 5 mg. It is noted that other dosing intervals and frequencies and dosage levels and formulations may be useful for reducing risk of or delaying development of disease, or treatment to reduce the rate of progression or halt progression, and optionally for prevention or reducing the risk of progression. Safety of the mAb is assessed by monitoring the subjects for reported AEs and by interpreting the results of the various laboratory tests for safety, which may include general blood chemistry, liver and kidney functions, and CBC including WBC differentials, as well as by comparing the frequency and patterns of AEs in the mAb treatment groups compared to that of the placebo group Immunological markers are measured for following the induction of Tregs, and any potential HAHA response. Efficacy is based on improvement in one or more of the following parameters: reduced levels of the liver enzymes ALT or AST, lower levels of glucose or triglycerides, and improved performance in glucose tolerance testing. The assessments for efficacy are ascertained for each subject by comparing values in efficacy parameters before mAb immunotherapy to those during and after immunotherapy, as well as by comparing overall changes in efficacy parameters among one or more of the mAb treatment groups compared to the placebo group.

It is to be understood that while the invention has been described in conjunction with the detailed description thereof, the foregoing description is intended to illustrate and not limit the scope of the invention, which is defined by the scope of the appended claims. Optionally any one or more embodiments, sub-embodiments and/or components of any embodiment may be combined. Other aspects, advantages, and modifications are within the scope of the following claims.

The invention claimed is:

1. A monoclonal antibody (mAb), or fragment thereof, that binds specifically to Cluster of Differentiation 3 (CD3), wherein said antibody comprises:
   i. a humanized framework comprising the heavy (H) chain variable (V) region set forth in SEQ ID NO: 7 with the mutations Q5V, A9S, A12K, R13K, K38R, R40A, Q43K, K66R, S75T, T83R, S87T, T108L and L109V, and the light kappa (K) chain V region set forth in SEQ ID NO: 8 with the mutations I10T, M11L, A13L, K18R, V19A, T22S, S40P, T42K, S43A, A60S, H61R, S70D, S72T, G77S, M78L, E79Q, A80P, A83F, S100G, L104V and N107K; and
   ii. the six CDRs set forth in SEQ ID NOs: 1-6.

2. The mAb according to claim 1 comprising a H chain constant domain selected from the group consisting of IgG1, IgG2, IgG3, IgG4, IgA, and IgM.

3. The mAb according to claim 1 comprising a human IgG4 constant region comprising a Ser241Pro mutation.

4. The mAb or fragment according to claim 1 comprising a heavy chain variable region set forth in SEQ ID NO: 9.

5. The mAb or fragment according to claim 1 comprising a light kappa chain V region set forth in SEQ ID NO: 10.

6. The mAb or fragment according to claim 1 comprising a heavy chain variable region set forth in SEQ ID NO: 9 and a light kappa chain V region set forth in SEQ ID NO: 10.

7. The mAb or fragment according to claim 1 comprising a full-length H chain according to SEQ ID NO: 11 and a full-length K chain according to SEQ ID NO: 12.

8. The mAb or fragment according to claim 1 comprising a H chain sequence having at least 95% identity to SEQ ID NO: 9 and a K chain sequence having at least 95% identity to SEQ ID NO: 10.

9. The mAb or fragment according to claim 1 comprising a VH chain encoded by a polynucleotide sequence comprising a sequence set forth in SEQ ID NO: 13, or such polynucleotide sequence having at least 70%, 75%, 80%, 85%, 90% or 95% identity while still encoding said polypeptide.

10. The mAb or fragment according to claim 1 comprising a VK chain encoded by a polynucleotide sequence comprising a sequence set forth in SEQ ID NO: 14, or such polynucleotide sequence having at least 70%, 75%, 80%, 85%, 90% or 95% identity while still encoding said polypeptide.

11. The mAb or fragment according to claim 1, comprising at least the V region.

12. The mAb or fragment according to claim 1, wherein the mAb or fragment is a mAb fragment.

13. The mAb fragment according to claim 12 comprising a heavy chain variable region set forth in SEQ ID NO: 9 or a light kappa chain V region set forth in SEQ ID NO: 10.

14. The mAb fragment according to claim 12 comprising a heavy chain variable region set forth in SEQ ID NO: 9 and a light kappa chain V region set forth in SEQ ID NO: 10.

15. The mAb fragment according to claim 12, comprising at least the V regions, wherein the mAb fragment is selected from the group consisting of: Fab, Fab', F(ab')2, scFv, and dsFv antibody.

16. The mAb or fragment of claim 1 which is a bispecific or multi-specific antibody.

17. A pharmaceutical composition comprising at least one mAb or fragment of claim 1.

18. The pharmaceutical composition according to claim 17 further comprising an excipient, diluent or carrier.

19. The pharmaceutical composition according to claim 17 formulated for oral or mucosal administration.

* * * * *